US010716872B2

(12) United States Patent
Kim et al.

(10) Patent No.: US 10,716,872 B2
(45) Date of Patent: Jul. 21, 2020

(54) COMPOSITION FOR PREVENTING ODORS CONTAINING ODORLESS MICROORGANISM

(71) Applicant: Hyundai Motor Company, Seoul (KR)

(72) Inventors: Ji Wan Kim, Gyeonggi-do (KR); Tae Hee Lee, Gyeonggi-Do (KR); So Yoon Park, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 51 days.

(21) Appl. No.: 15/942,896

(22) Filed: Apr. 2, 2018

(65) Prior Publication Data

US 2019/0216965 A1 Jul. 18, 2019

Related U.S. Application Data

(62) Division of application No. 14/653,977, filed as application No. PCT/KR2013/012052 on Dec. 23, 2013, now abandoned.

(30) Foreign Application Priority Data

Dec. 21, 2012 (KR) .................. 10-2012-0150630

(51) Int. Cl.
A61L 9/00 (2006.01)
A61L 9/01 (2006.01)
F25B 39/02 (2006.01)
A01N 63/00 (2020.01)
C12N 1/20 (2006.01)

(52) U.S. Cl.
CPC ............... *A61L 9/00* (2013.01); *A01N 63/00* (2013.01); *A61L 9/01* (2013.01); *C12N 1/20* (2013.01); *F25B 39/02* (2013.01)

(58) Field of Classification Search
CPC .. A61L 9/00; A61L 9/01; A01N 63/00; C12N 1/20; F25B 39/02
See application file for complete search history.

(56) References Cited

U.S. PATENT DOCUMENTS

| 5,366,004 A | 11/1994 | Garner et al. |
| 6,051,423 A | 4/2000 | Ceri et al. |
| 8,920,651 B2 | 12/2014 | Jones et al. |
| 2011/0233125 A1 | 9/2011 | Jones et al. |

FOREIGN PATENT DOCUMENTS

| CN | 102114258 A | 7/2011 |
| EP | 2 239 319 A1 | 10/2010 |
| EP | 2937414 A1 | 10/2015 |
| JP | H09-511941 A | 12/1997 |
| JP | 2004-505613 A | 2/2004 |
| JP | 2004-344122 A | 12/2004 |
| JP | 3886152 B2 | 2/2007 |
| JP | 2009-093675 A | 4/2009 |
| JP | 2016-504031 A | 2/2016 |
| JP | 2016-163551 A | 9/2016 |
| KR | 1998-0003946 A | 3/1998 |
| KR | 1998-0033946 A | 8/1998 |
| KR | 2002-0042883 A | 6/2002 |
| KR | 2003-0057543 A | 7/2003 |
| KR | 20030086477 A | * 11/2003 |
| KR | 2011-0043256 A | 4/2011 |
| KR | 10-2012-0020309 A | 3/2012 |
| KR | 2012-0093641 A | 8/2012 |
| KR | 101438969 B1 | 9/2014 |
| KR | 2015-0067563 A | 6/2015 |
| KR | 101543210 B1 | 8/2015 |
| KR | 2015-0105637 A | 9/2015 |
| RU | 2414508 C2 | 3/2011 |
| WO | 96/14882 A1 | 5/1996 |
| WO | 2011/059963 A1 | 5/2011 |
| WO | 2012/111875 A1 | 8/2012 |
| WO | 2014/098543 A1 | 6/2014 |

OTHER PUBLICATIONS

Simmons, R. B. et al., The Occurrence and Persistence of Mixed Biofilms in Automobile Air Conditioning Systems, 1999, Current Microbiology, 39, 141-145 (Year: 1999).*
Garrett, T. R. et al., Bacterial adhesion and biofilms on surfaces, 2008, Progress in Natural Science, 18, 1049-1056 (Year: 2008).*
International Search Report, dated Mar. 26, 2014, in corresponding PCT/KR2013/012052.
Simmons, R.B. et al., "The Occurrence and Persistence of Mixed Biofilms in Automobile Air Conditioning Systems", Current Microbiology, Co., vol. 39 (1999) pp. 141-145.
McNevin et al., "Biofiltration as an adour abatement strategy", (2000) Biochemical Engineering Journval, vol. 5, pp. 231-242.
Kato, Y. et al, "*Methylobacterium persicinum* sp. nov., *Methylobacterium komagatae* sp. nov., *Methylobacterium brachiatum* sp. nov., *Methylobacterium tardum* sp. nov. and *Methylobacterium gregans* sp. nov., isolated from freshwater", International Journal of Systematic and Evolutionary Microbiology (2008) 58, 1134-1141.
Kang, Y.S. et al, "*Methylobacterium plantani* sp. nov., isolated from a leaf of the tree *Platanus orientalis*", International Journal of Systematic and Evolutionary Microbiology (2007) 57, 2849-2853.

(Continued)

*Primary Examiner* — Louise W Humphrey
*Assistant Examiner* — Anjali Ajit Hirani
(74) *Attorney, Agent, or Firm* — Mintz Levin Cohn Ferris Glovsky and Poppeo, P.C.; Peter F. Corless

(57) ABSTRACT

The present invention relates to a composition for preventing odors containing odorless microorganisms or a culture thereof. The present invention also relates to a method for preventing odors including coating the composition for preventing odors. When a biofilm is formed by coating an object offensive odor-generating microorganisms can inhabit with the composition for preventing odors of the present invention, odors can be effectively prevented by significantly preventing the inflow and inhabitation of outside microorganisms that may generate offensive odors.

12 Claims, 18 Drawing Sheets

Specification includes a Sequence Listing.

(56) References Cited

OTHER PUBLICATIONS

Xue et al. (2012) "Geosmin Degradation by Seasonal Biofilm from a Biological Treatment Facility", Environmental Science and Pollution Research, 19(3):700-707.
Baek, et al., "Evaluation of Microbes Through Biological Activated Carbon & Microfiltration Within Water Treatment Processes", Master's Thesis, Yonsei Graduate School, Jan. 16, 2015, 72 pages.
Reasoner, et al., "A New Medium for the Enumeration and Subculture of Bacteria from Potable Water", Applied Environmental Microbiology, Jan. 1985, 49(1):1-7.
Schmidt, et al., "Characterization and Control of the Microbial Community Affiliated with Copper or Aluminum Heat Exchangers of HVAC Systems", Current Microbiology, Aug. 2012, 65(2):141-149.

* cited by examiner

SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ctacggcaag gcgacgctga cg   22

COMPOSITION FOR PREVENTING ODORS CONTAINING ODORLESS MICROORGANISM

CROSS-REFERENCE TO RELATED APPLICATION

This application is a divisional application of U.S. patent application Ser. No. 14/653,977 filed Jun. 19, 2015 which is a U.S. National Phase Entry of the International Patent Application No. PCT/KR2013/012052 filed Dec. 23, 2013, which also claims priority under 35 U.S.C. § 119 to Korean Patent Application No. 10-2012-0150630, filed on Dec. 21, 2012, in the Korean Intellectual Property Office, the disclosure of which is incorporated herein by reference in its entirety.

INCORPORATION-BY-REFERENCE OF A SEQUENCE LISTING

The sequence listing contained in the file "058268_530D0101US_Sequence_Listing.txt", created on Jun. 2, 2020, file size 589 bytes, is incorporated by reference in its entirety herein.

BACKGROUND

(a) Technical Field

The present invention relates to a composition for preventing odors containing odorless microorganisms or a culture thereof and a method for preventing odors using the same.

(b) Background Art

Clean air is recognized as an integral component in human health and well-being. Offensively smelling or polluted air severely spoils a pleasant environment. For example, unsatisfactory indoor air quality under an airtight condition is caused by two important factors. One is the air pollutants generated directly from the materials that constitute the airtight environment (e.g., building, vehicle, etc.) and the other is the odor generated by human activities or caused by external substances.

An air-conditioning system refers to a system designed to decrease indoor temperature and optimize the indoor environment in buildings, vehicles, trains, ships, airplanes, etc. for the purpose of conditioning the temperature, humidity, flow rate and cleanness of air. With improvement in the standard of living, the use of the air-conditioning system has been increasing gradually. Although there has been much improvement in the basic function of the air-conditioning system, a lot of problems still remain to be solved in the environmental aspect for indoor air quality.

The cause of the odor of the air-conditioning system, particularly an air conditioner, has been known to be the metabolites produced by molds and bacteria. However, it has not been specifically identified yet which molds and bacteria produce how much such metabolites.

In an air-conditioning system, all the air that has passed through a blower passes an evaporator core. During the heat exchange between a cold refrigerant and the air, condensation of water occurs on the surface of the evaporator core due to temperature difference. When the condensation of water continues, an environment favorable for inhabitation and proliferation of molds and bacteria is created on the evaporator core. If molds and bacteria proliferate on the evaporator core exposed to the external air, microbial volatile organic compounds (mVOCs) are produced as metabolites by the microorganisms. Thus, when the air that has passed through the evaporator core is blown indoors, the indoor may be exposed to offensive odor due to the volatile organic compounds produced by the molds and bacteria after long-term use.

After long-term use, the surface of the evaporator core is covered with a biofilm, which consists of bacteria, cell clusters and extracellular polymeric substances (EPS). EPS include various components such as proteins, polysaccharides, polyuronic acids, nucleic acids, lipids, etc. On the surface of the evaporator core, various bacteria and molds proliferate with the biofilm as nutrients and produce various microbial volatile organic compounds (mVOCs) as metabolites, which are known as the cause of the foul odor of the air conditioner.

Although various types of aromatics are commercially available for removing such offensive odor, they do not fundamentally remove the molds and bacteria proliferating on the evaporator core but merely dilute the unpleasant odor temporarily. Also, the antibacterial agents that are commercially available at present are not developed to specifically act on particular molds or bacteria proliferating on the evaporator core but they are used because they are considered to have antibacterial effects against common pathogens.

The inventors of the present invention have disclosed in Korean Patent Publication No. 10-2012-0020309 a method for manufacturing an evaporator core coated with a biofilm formed of specific microorganisms that are odorless or fragrant to prevent attachment and growing of bacteria and molds that cause offensive odor on the evaporator core.

However, it was not identified which bacteria are such odorless microorganisms. Also, it was not clearly demonstrated whether they can survive on the evaporator core after being coated thereon and can prevent the inhabitation of microorganisms causing offensive odor and therefore can prevent the offensive odor.

The above description of the background art is intended only to improve understanding of the background of the present invention and should not be construed as recognizing that the above-described technologies are known to those having ordinary skill in the technical field to which the present invention pertains.

SUMMARY

The inventors of the present invention have made efforts to find a method for effectively controlling microorganisms causing offensive odor using odorless microorganisms. As a result, they have successfully screened 13 kinds of microorganisms which do not cause offensive odor in an air-conditioning system and have confirmed that, when a biofilm is formed using them or a combination of them, the growth of offensive odor-causing microorganisms can be prevented and thus offensive odor can be prevented.

The present invention is directed to providing a composition for preventing odors, which contains odorless microorganisms or a culture thereof.

The present invention is also directed to providing an evaporator core coated with the composition for preventing odors.

The present invention is also directed to providing a method for manufacturing an odorless evaporator core which does not cause odor in an air-conditioning system, which includes coating the composition for preventing odors on an evaporator core.

The present invention is also directed to providing a method for preventing odors from an air-conditioning system, which includes coating the composition for preventing odors on an evaporator core.

The present invention is also directed to providing a method for checking odors from an air-conditioning system, which includes coating the composition for preventing odors on an evaporator core.

The present invention is also directed to providing odorless microorganisms for coating an evaporator core for preventing odors from an air-conditioning system.

Other purposes and advantages of the present invention will be apparent from the following detailed description, drawings and claims.

In an aspect, the present invention provides a composition for preventing odors, which contains odorless microorganisms or a culture thereof.

The inventors of the present invention have made efforts to find a method for effectively controlling microorganisms causing offensive odor using odorless microorganisms. In particular, they have endeavored to fundamentally eradicate the cause of offensive odors from an air-conditioning system. As a result, they have successfully screened 13 kinds of microorganisms which do not cause offensive odor in an air-conditioning system and have confirmed that, when a biofilm is formed using them or a combination of them, the growth of offensive odor-causing microorganisms can be prevented and thus offensive odor can be prevented.

In the present invention, the term "air-conditioning system" refers to a system which maintains temperature, humidity, cleanness, flow, etc. of air inside a space which is entirely or partially isolated from the external environment. As a preferred example, the isolated space may be an indoor space which is entirely or partially isolated from outside, such as inside a building, vehicle, train, ship, airplane, etc. As a preferred example, the air-conditioning system may be an air conditioner.

In an air-conditioning system, all the air that has passed through a blower passes an evaporator core. On the surface of the evaporator core, an environment favorable for growth of microorganisms is created as condensation of water due to temperature difference continues. As a result, a biofilm is formed with time. The microorganisms metabolize various substances floating in the air indoors or outdoors as nutrients and produce various microbial volatile organic compounds (mVOCs) as metabolites, which give off foul odor.

The biofilm is a group of living microorganisms enclosed in a membrane. The membrane protects the microorganisms from external environment and supplies nutrients. The membrane is composed of extracellular polymeric substances (EPS), which include various components such as proteins, polysaccharides, polyuronic acids, nucleic acids, lipids, etc. On the surface of the evaporator core, a variety of microorganisms proliferate using them as nutrients and produce metabolites which give off offensive odor.

The inventors of the present invention have screened microorganisms which do not cause offensive odor from the evaporator core and, through culturing, have isolated dominant strains that form colonies from the microorganisms. The dominant strains may be isolated and cultured according to various methods known in the related art and the dominant microorganisms may be screened, for example, based on dilution ratios or morphological characteristics such as the color, size, shape, etc. of the colonies.

The dominant microorganisms include *Methylobacterium, Acinetobacter, Bacillus, Brevibacillus, Deinococcus, Pseudomonas, Sphingomonas* or *Flavobacterium*, specifically *Methylobacterium aquaticum, Methylobacterium brachiatum, Methylobacterium platani, Acinetobacter johnsonii, Bacillus vietnamensis, Brevibacillus invocatus, Deinococcus ficus, Leifsonia soli, Pseudomonas nitroreducens, Sphingomonas aquatilis, Methylobacterium komagatae, Deinococcus apachensis* or *Flavobacterium oceanosedimentum.*

These microorganisms were deposited in the Korean Culture Center of Microorganisms on Nov. 14, 2012 or Dec. 10, 2013 and were given the following accession numbers: *Methylobacterium aquaticum* HKMC-1 (Accession number: KCCM11325P), *Methylobacterium brachiatum* HKMC-2 (Accession number: KCCM11326P), *Methylobacterium platani* HKMC-3 (Accession number: KCCM11327P), *Acinetobacter johnsonii* HKMC-4 (Accession number: KCCM11328P), *Bacillus vietnamensis* HKMC-5 (Accession number: KCCM11329P), *Brevibacillus invocatus* HKMC-6 (Accession number: KCCM11330P), *Deinococcus ficus* HKMC-7 (Accession number: KCCM11331P), *Leifsonia soli* HKMC-8 (Accession number: KCCM11332P), *Pseudomonas nitroreducens* HKMC-9 (Accession number: KCCM11333P), *Sphingomonas aquatilis* HKMC-10 (Accession number: KCCM11334P), *Methylobacterium komagatae* HKMC-11 (Accession number: KCCM11335P), *Deinococcus apachensis* HKMC-12 (Accession number: KCCM11499P) and *Flavobacterium oceanosedimentum* HKMC-13 (Accession number: KCCM11500P).

The microorganisms may be contained in the composition for preventing odors either alone or in combination other microorganisms.

The composition for preventing odors of the present invention may be used to prevent the inhabitation of offensive odor-generating microorganisms and/or the offensive odors generated by them. That is to say, the composition of the present invention may be used to prevent the inhabitation of offensive odor-generating microorganisms by coating on or spraying to all or specific parts of offensive odor-generating apparatuses (e.g., air-conditioning system, waste water treatment unit, etc.), articles (e.g., waste basket, toilet bowl, etc.), animals (e.g., contaminated livestock, etc.) or human bodies (e.g., mouth, diabetic foot, etc.).

The composition for preventing odors of the present invention may further contain various medium components known in the related art to enhance biofilm formation on the different objects. The medium components may include, for example, agar, gelatin, alginate, carageenan or pectin. Specifically, PTYG medium, R2A medium or LB medium may be used for an evaporator core in an air-conditioning system.

The composition for preventing odors of the present invention may further contain, in addition to the odorless microorganisms, an aromatic, a sterilizer, an antimicrobial agent, etc. to prevent offensive odors or to prevent or remove offensive odor-generating microorganisms.

In a preferred exemplary embodiment of the present invention, the composition of the present invention is for preventing odors from an air-conditioning system.

The air-conditioning system to which the composition of the present invention is applicable may be installed in buildings, vehicles, trains, ships, airplanes, etc. for the purpose of conditioning the temperature, humidity, flow rate or cleanness of air.

The object on which the biofilm of the present invention is coated may be an air-conditioning system. The air-conditioning system includes a compressor, a blower, an evaporator core, etc. Specifically, the object on which the biofilm of the present invention is coated may be an evaporator core.

Specifically, an environment favorable for inhabitation and proliferation of microorganisms is created on the surface of the evaporator core in the air-conditioning system due to heat exchange of air. With time, the microorganisms adhering on the surface form a stable biofilm which is difficult to be removed. That is to say, the odorless microorganisms can be proliferated in advance such that the inhabitation of offensive odor-generating microorganisms can be prevented.

The inventors of the present invention have found out that a biofilm consisting only of odorless microorganisms which are dominant species or have superior viability can be formed on the evaporator core by coating them in advance on the evaporator core of the air-conditioning system and, thereby, offensive odors and the proliferation and inhabitation of other offensive odor-generating microorganisms can be significantly prevented (Examples 9-14).

In another aspect, the present invention provides an evaporator core coated with the composition for preventing odors and a method for manufacturing the same.

A fin of the evaporator core is made of aluminum or an aluminum alloy, and the evaporator core is manufactured using antibacterial-treated aluminum or a non-antibacterial-treated aluminum alloy. However, the material of the evaporator core is not limited to the aluminum or the aluminum alloy. In general, the evaporator core may be manufactured from any metal having good thermal conductivity and excellent corrosion resistance, such as copper, in addition to the aluminum or an alloy thereof. In an electric vehicle, for example, a heat exchanger may be coupled with a Peltier device. Like this, any material can be used as long as a structure allowing for easy heat exchange can be achieved.

The composition for preventing odors containing odorless microorganisms or a culture thereof may be coated on the evaporator core according to various methods known the related art (e.g., spraying, coating, immersion). Preferably, the evaporator core may be immersed in a culture of the odorless microorganisms such that the odorless microorganisms can be uniformly coated on the fin inside the evaporator core. The coating may be carried out once or several times.

The culture of the odorless microorganisms may have an optical density (O.D.) of 0.3-0.9, more preferably 0.4-0.8.

When the microorganism culture having an O.D. value of 0.3-0.9 is used, the microorganisms may be coated at a concentration of $10^4$-$10^8$ CFU/g. And, when the microorganism culture having an O.D. value of 0.4-0.89 is used, the microorganisms may be coated at a concentration of $10^5$-$10^7$ CFU/g. Considering that the concentration of microorganisms present on the evaporator core in a used vehicle is about $10^6$ CFU/g, the microorganisms may be preferably coated at a concentration of $10^5$-$10^7$ CFU/g using a microorganism culture having an O.D. value of 0.4-0.8.

The coated odorless microorganisms can form a biofilm which is stable for a long time (30 days or longer, 60 days or longer or 90 days or longer) by being uniformly distributed on and inhabiting the evaporator core surface (Examples 11-13).

In another aspect, the present invention provides a method for preventing odors from an air-conditioning system, including: coating the composition for preventing odors on an evaporator core.

The inventors of the present invention have conducted experiments after installing a jig on a vehicle roof and then mounting the evaporator core coated with the composition of the present invention thereon in order to investigate whether the evaporator core can maintain the population of odorless microorganisms under an outdoor air condition and prevent the inhabitation of other offensive odor-generating microorganisms. As a result, it was found that the initially coated population of the odorless microorganisms was maintained for 60 days and no exogenous microorganisms that may generate offensive odor were detected (Example 14).

Accordingly, when a biofilm is formed by coating the composition for preventing odors containing odorless microorganisms of the present invention, the inflow and inhabitation of exogenous microorganisms that may generate offensive odors can be significantly prevented and, thus, the offensive odors from an air-conditioning system can be effectively prevented.

In another aspect, the present invention provides a method for checking odors from an air-conditioning system, including coating the composition for preventing odors on an evaporator core.

Whether the microorganisms contained in the composition for preventing odors actually generate odors may be dependent on the components of nutrition source which the microorganisms metabolize. Therefore, it is important that the microorganisms not generate odors when the nutrition sources in the related industrial fields are supplied.

In case of an air-conditioning system, microorganisms metabolize various substances floating in the air indoors and outdoors as nutrients. That is to say, indoor or outdoor air contaminants or exhaust gas components (petroleum fuels such as gasoline, diesel oil, LPG, etc.) are the nutrition sources of the microorganisms. Accordingly, it can be checked in advance whether odors will be generated from an air-conditioning system under the actual industrial setting by introducing these nutrition sources to the evaporator core coated with the microorganisms.

In another aspect, the present invention provides *Methylobacterium aquaticum* HKMC-1 (Accession number: KCCM11325P), *Methylobacterium brachiatum* HKMC-2 (Accession number: KCCM11326P), *Methylobacterium platani* HKMC-3 (Accession number: KCCM11327P), *Acinetobacter johnsonii* HKMC-4 (Accession number: KCCM11328P), *Bacillus vietnamensis* HKMC-5 (Accession number: KCCM11329P), *Brevibacillus invocatus* HKMC-6 (Accession number: KCCM11330P), *Deinococcus ficus* HKMC-7 (Accession number: KCCM11331P), *Leifsonia soli* HKMC-8 (Accession number: KCCM11332P), *Pseudomonas nitroreducens* HKMC-9 (Accession number: KCCM11333P), *Sphingomonas aquatilis* HKMC-10 (Accession number: KCCM11334P), *Methylobacterium komagatae* HKMC-11 (Accession number: KCCM11335P), *Deinococcus apachensis* HKMC-12 (Accession number: KCCM11499P) or *Flavobacterium oceanosedimentum* HKMC-13 (Accession number: KCCM11500P) as microorganisms for coating an evaporator core to prevent odors from an air-conditioning system.

These microorganisms may be used for coating an evaporator core to prevent odors from an air-conditioning system either alone or in combination.

The features and advantages of the present disclosure may be summarized as follows:
  (i) The present invention provides a composition for preventing odors, which contains odorless microorganism or a culture thereof.
  (ii) The present invention also provides an evaporator core which is coated with the composition for preventing odors and a method for manufacturing the same.

(iii) In addition, the present invention provides a method for preventing odors, which includes coating the composition for preventing odors on an evaporator core.

(iv) When a biofilm is formed by coating the composition for preventing odors of the present invention on an object that offensive odor-generating microorganism may inhabit, offensive odors may be prevent effectively by significantly preventing the inflow and inhabitation of the offensive odor-generating exogenous microorganisms.

DETAILED DESCRIPTION

Figure 1:
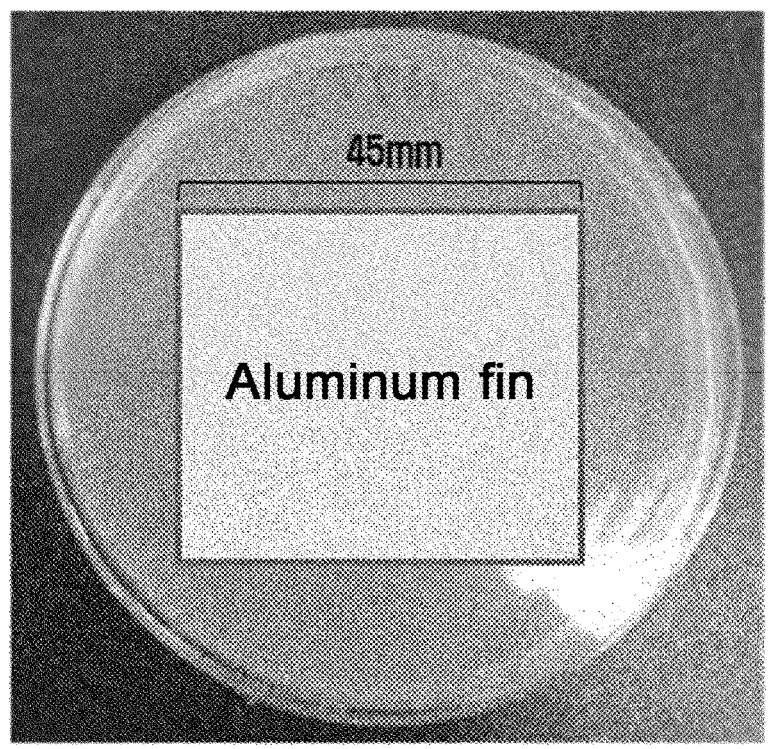
FIG. 1 shows a Petri dish in which a sterilized aluminum fin is dipped in a nutrient medium for inoculation with odorless microorganisms.

Hereinafter, the present invention will be described in more detail through examples. The following examples are for illustrative purposes only and it will be apparent to those or ordinary skill in the related art that the scope of this invention is not limited by the examples.

EXAMPLES

Example 1

Used Vehicles Giving Off Offensive Odors

TABLE 1

| No. | Vehicle | Sample type |
| --- | --- | --- |
| 1 | Vehicle A | Evaporator core |
| 2 | Vehicle B | Evaporator core |
| 3 | Vehicle C | Evaporator core |
| 4 | Vehicle D | Evaporator core |
| 5 | Vehicle E | Evaporator core |

Evaporator core samples were taken from the evaporator cores mounted in 5 used vehicles (vehicles A-E) giving off offensive odors.

Example 2

Preparation of Evaporator Core Samples

The evaporator core samples taken from the evaporator cores of the used vehicles A-E were stored in sealed polyethylene bags at 4° C. until use. For isolation and culturing of microorganisms, 5 g of fin samples were taken from each evaporator core at various parts including front and rear parts using sterilized long-nose pliers and then mixed before use.

Example 3

Detachment of Microorganisms From Evaporator Cores

Microorganisms were detached from the evaporator cores as follows.
① The samples taken from the evaporator core were mixed and put in a mixer.
② 200 mL of sterilized 1× phosphate buffed saline (PBS) were added to the mixer.
③ The mixed samples and the PBS were mixed for 30 seconds.
④ The mixer was left on ice for 1 minute.
⑤ The steps ③ and ④ were repeated 2 more times.
⑥ The resulting suspension was centrifuged at 4° C. for 3 minutes at 13000 rpm.
⑦ Only the supernatant was taken and transferred to a fresh tube.
⑧ The surface of the evaporator core from which the samples were taken was wiped several times with a sterilized cotton swab soaked with the supernatant.
⑨ The head of the cotton swab was put in the supernatant and then vortexed.
⑩ The precipitate obtained in the step ⑥ and the mixture obtained in the ⑨ were mixed and used as an inoculation solution.

Microorganisms were physically detached from the evaporator cores of the vehicles A-E through the steps ①-⑩.

Example 4

Isolation and Culturing of Microorganisms

Aerobic heterotrophic bacteria usually called normal bacteria were isolated from the air conditioner by culturing on a heterotrophic plate. PTYG agar medium and R2A agar medium were used as complex nutrient media to isolate the normal bacteria. The PTYG agar medium was prepared by adding 0.25 g of peptone (Difco), 0.25 g of triptone (Difco), 0.5 g of yeast extract (Difco), 0.5 g of glucose (Difco), 30 mg of $MgSO_4$ (Sigma), 3 mg of $CaCl_2$ (Sigma) and 15 g of Bacto agar (Difco) to 980 mL of distilled water and sterilizing at 121° C. for 15 minutes under high pressure after adjusting pH to 7.0. The R2A agar medium was prepared by adding 0.5 g of yeast extract (Difco), 0.5 g of proteose peptone No. 3 (Difco), 0.5 g of casamino acids (Difco), 0.5 g of dextrose (Difco), 0.5 g of soluble starch (Difco), 0.3 g of sodium pyruvate (Difco), 0.3 g of dipotassium sulfate (Difco), 0.05 g of magnesium sulfate (Difco) and 15 g of Bacto agar (Difco) to 980 mL of distilled water and sterilizing at 121° C. for 15 minutes under high pressure after adjusting pH to 7.2. Three kinds of antibiotics (Table 2) were used to isolate the non-dominant normal bacteria. Each antibiotic was inoculated at about 50° C. after filter-sterilizing the medium to a concentration of 100 ppm.

TABLE 2

| No. | Antibiotic | Type | Manufacturer |
|---|---|---|---|
| 1 | Kanamycin | Aminoglycoside | Sigma |
| 2 | Ampicillin | beta-lactam | Sigma |
| 3 | Chloramphenicol | Chloramphenicol | Sigma |

Example 5

Isolation and Culturing of Fungi (Molds)

Fungi (molds) were isolated from the air conditioner by culturing on an aerobic plate using nutrient media. Potato dextrose agar medium and malt extract agar medium were used to isolate the fungi (molds). The potato dextrose agar medium was prepared by adding 4 g of potato starch (Difco), 20 g of dextrose (Difco) and 15 g of Bacto agar (Difco) to 980 mL of distilled water and sterilizing at 121° C. for 15 minutes under high pressure after adjusting pH to 5.1. The malt extract agar medium was prepared by adding 20 g of malt extract (Difco) and 15 g (Difco) of Bacto agar to 980 mL of distilled water and sterilizing at 121° C. for 15 minutes under high pressure after adjusting pH to 5.0.

A 90 mm×15 mm Petri dish was used to culture the fungi and the cultured fungi were isolated using a 60 mm×15 mm Petri dish.

Example 6

Isolation and Culturing of Dominant Strains

Dominant strains were isolated and cultured based on dilution ratios or morphological characteristics such as the color, size, shape, etc. of the colonies as follows.
① Molds and bacteria were separated from the culture media.
② The bacteria exhibiting different morphologies were separated by inoculating to complex media using a loop.
③ From the inoculated media, the bacterial culture showing the best growth was selected and subcultured.
④ The molds were inoculated to complex media after removing the hypha end portions using a scalpel.
⑤ From the inoculated media, the mold culture showing the best growth was selected and subcultured.

Example 7

Genetic Characterization of Dominant Bacteria

Fingerprinting Based on Analysis of REP-PCR Patterns

REP-PCR is a molecular biological fingerprinting technique for structural analysis of bacterial chromosomes, which allows distinguishment of different bacterial strains. Genetic characterization was carried out by REP-PCR as follows.
(1) Cell Lysis
① 2.5 µL of a Lyse-N-Go PCR reagent (Thermo) was added to a PCR tube.
② A colony was pipetted onto the tube on a clean bench. During the pipetting, caution was made such that the resulting solution did not become turbid.
③ Culturing was performed on a PCR machine according to the manufacturer's instructions.
④ Cell lysis was conducted according to the lysis protocol described in Table 3. At the 9th cycle, the temperature was held at 80° C.

TABLE 3

| Cycle | Temperature (° C.) | Time (seconds) |
|---|---|---|
| 1 | 65 | 30 |
| 2 | 8 | 30 |
| 3 | 65 | 90 |
| 4 | 97 | 180 |
| 5 | 8 | 60 |
| 6 | 65 | 180 |
| 7 | 97 | 60 |
| 8 | 65 | 60 |
| 9 | 80 | hold |

(2) PCR Reaction

Using a PCR reagent prepared as described in Table 4, PCR amplification was carried out by conducting pre-denaturation at 94° C. for 7 minutes and repeating 33 cycles of denaturation at 92° C. for 1 minute, annealing at 51.5° C. for 1 minute and extension at 65° C. for 8 minutes, as described in Table 5.

TABLE 4

| | | |
|---|---|---|
| ① | dNTP (2.5 mM each) | 12.5 µL |
| ② | Gitschier buffer | 5.0 µL |
| ③ | DMSO (100%) | 2.5 µL |
| ④ | Autoclaved 3° D.W. | 0.3 µL |
| ⑤ | BOXA1R primer (50 pmole/µL) 5'CTACGGCAAGGCGACGCTGACG | 1.0 µL |
| ⑥ | BSA (10 mg/mL) | 0.4 µL |
| ⑦ | Bacterial DNA | 2.5 µL |
| ⑧ | Taq polymerase (Roche) (5 U/µL) | 0.8 µL |

TABLE 5

| Step 1 | 93° C. | 7 min |
|---|---|---|
| Step 2 | 92° C. | 1 min |

TABLE 5-continued

| Step 3 | 51.5° C. | 1 min |
|---|---|---|
| Step 4 | 65° C. | 8 min |
| Steps 2, 3, 4: additional 33 cycles | | |
| Step 6 | 65° C. | 16 min |
| Step 7 | 4° C. | |

(3) Gel Electrophoresis

The PCR-amplified DNA fragments were loaded onto 1.2-1.5% agarose gel supplemented with EtBr after mixing a 6× dye with the sample at a ratio of 1:5. Since most PCR products were in the range of 100-1000 bp, they were loaded tougher with 100 bp ladders. Then, electrophoresis was carried out as slowly as possible (50 V) such that bromophenol blue and xylene cyanol dyes moved halfway of the entire gel. The strains exhibiting the same DNA pattern on the gel were regarded as the same strains.

(4) Isolation of Dominant Bacteria Based on 16S rRNA Gene Analysis

The 16S ribosomal ribonucleic acid (rRNA) gene is used to genetic identification of bacteria. The bacteria differentiated by REP-PCR can be identified in the levels of genus and species thereby. 16S rRNA is an RNA which constitutes a ribosome by interacting with various proteins. Since the full sequences or base sequences of oligonucleotides are known for more than 2000 bacterial species, bacteria can be grouped based on the similarity of the 16S rRNA gene. Because the difference in the base sequence of the 16S rRNA gene is much smaller than those of the base sequences of other genes in the genome, the similarity of the base sequence of 16S rRNA is considered as a measure of the evolutionary distance between organisms. The identification of microorganisms, in particular, industrially useful microorganisms, based on the similarity of the base sequence of 16S rRNA gene fragments has been used as a typical identification method together with fatty acid analysis and carbohydrate assimilation profiling.

<16S rRNA PCR>

PCR conditions (total 50 μL): A mixture (44.5 μL) of the solutions described in Table 6, except for DNA and Taq, was added to the lysis solution described above. Subsequently, PCR amplification was carried out by conducting pre-denaturation at 94° C. for 5 minutes and repeating 29 cycles of denaturation at 94° C. for 1 minute, annealing at 55° C. for 1 minute and extension at 72° C. for 1 minute and 30 seconds, as described in Table 7.

TABLE 6

| Autoclaved 3° D.W. | 22 μL |
|---|---|
| 10x buffer (Roche) | 5 μL |
| dNTP (Roche, 2.5 mM) | 5 μL |
| DMSO | 5 μL |
| BSA (10 mg/mL) | 2.5 μL |
| 27mf (20 pmole/μL) | 2.5 μL |
| 1492r (20 pmole/μL) | 2.5 μL |
| DNA | 5 μL |
| Taq (Roche) | 0.5 μL |

TABLE 7

| Step 1 | 94° C. | 5 min |
|---|---|---|
| Step 2 | 94° C. | 1 min |

TABLE 7-continued

| Step 3 | 55° C. | 1 min |
|---|---|---|
| Step 4 | 72° C. | 1 min 30 sec |
| Go to step 2: additional 29 cycles | | |
| Step 6 | 72° C. | 10 min |
| Step 7 | 4° C. | hold |

(5) PCR Purification

The 16S rRNA PCR products were purified using a QIAquick PCR purification kit.

① The PCR products were added to a 5×PB buffer.
② The resulting solution was transferred to a QIAquick column.
③ For DNA binding, the solution was centrifuged for 1 minute.
④ For washing, 750 μL of PE buffer was added to the QIAquick column and centrifugation was performed for 1 minute.
⑤ Centrifugation was performed for 1 minute.
⑥ The resulting solution was transferred to a fresh QIAquick column.
⑦ For DNA extraction, 30 μL of EB buffer was added and the resulting solution was allowed to stand for 1 minute.
⑧ After performing centrifugation for 1 minute, the DNA dissolved in EB was collected in a tube.

(6) Isolated Microorganisms and Characteristics Thereof

<Microorganism 1>

1. Name of microorganism: HKMC-1
Genus: *Methylobacterium*
Species: *aquaticum*
Accession number: KCCM11325P (2012.11.14)
Depository: Korean Culture Center of Microorganisms
Depository Address: 361-221, Yurim B/D Hongje-1-dong, Seodaemun-gu, SEOUL, 120-091, Republic of Korea 2. Reconstitution Condition
  a. Reconstituting Agent
  (1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
  (2) pH: 7.0
  (3) Sterilizing condition: 20 minutes at 121° C.
  b. Culturing at 28° C. for 7 days 3. Medium
  (1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
  (2) pH: 7.0
  (3) Sterilizing condition: 20 minutes at 121° C.

4. Culturing Condition
  a. Aerobic/anaerobic: aerobic
  b. Temperature: 28° C.
  c. Culturing with or without agitation (liquid or solid)

5. Storing Condition
Temperature: −70° C.

<Microorganism 2>

1. Name of microorganism: HKMC-2
Genus: *Methylobacterium*
Species: *brachiatum*
Accession number: KCCM11326P (2012.11.14)
Depository: Korean Culture Center of Microorganisms
Depository Address: 361-221, Yurim B/D Hongje-1-dong, Seodaemun-gu, SEOUL, 120-091, Republic of Korea 2. Reconstitution Condition
a. Reconstituting Agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 3>
1. Name of microorganism: HKMC-3
Genus: *Methylobacterium*
Species: *platani*
Accession number: KCCM11327P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 4>
1. Name of microorganism: HKMC-4
Genus: *Acinetobacter*
Species: *johnsonii*
Accession number: KCCM11328P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting Agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 5>
1. Name of microorganism: HKMC-5
Genus: *Bacillus*
Species: *vietnamensis*
Accession number: KCCM11329P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 6>
1. Name of microorganism: HKMC-6
Genus: *Brevibacillus*
Species: *invocatus*
Accession number: KCCM11330P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days 3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 7>
1. Name of microorganism: HKMC-7
Genus: *Deinococcus*
Species: *ficus*
Accession number: KCCM11331P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 8>
1. Name of microorganism: HKMC-8
Genus: *Leifsonia*
Species: *soli*
Accession number: KCCM11332P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 9>
1. Name of microorganism: HKMC-9
Genus: *Pseudomonas*
Species: *nitroreducens*
Accession number: KCCM11333P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 10>
1. Name of microorganism: HKMC-10
Genus: *Sphingomonas*
Species: *aquatilis*
Accession number: KCCM11334P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.

c. Culturing with or without agitation (liquid or solid)
5. Storing Condition
Temperature: −70° C.
<Microorganism 11>
1. Name of microorganism: HKMC-11
Genus: *Methylobacterium*
Species: *komagatae*
Accession number: KCCM11335P (2012.11.14)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.
<Microorganism 12>
1. Name of microorganism: HKMC-12
Genus: *Deinococcus*
Species: *apachensis*
Accession number: KCCM11499P (2013.12.10)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

<Microorganism 13>
1. Name of microorganism: HKMC-13
Genus: *Flavobacterium*
Species: *oceanosedimentum*
Accession number: KCCM11500P (2013.12.10)
Depository: Korean Culture Center of Microorganisms
Depository Address: 361-221, Yurim B/D Hongje-1-dong, Seodaemun-gu, SEOUL, 120-091, Republic of Korea
2. Reconstitution Condition
a. Reconstituting agent
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
b. Culturing at 28° C. for 7 days
3. Medium
(1) Composition: PTYG medium (per 1 L of medium, 0.25 g of peptone, 0.25 g of triptone, 0.5 g of yeast extract, 0.5 g of glucose, 30 mg of $MgSO_4$ and 3 mg of $CaCl_2$) or R2A medium.
(2) pH: 7.0
(3) Sterilizing condition: 20 minutes at 121° C.
4. Culturing Condition
a. Aerobic/anaerobic: aerobic
b. Temperature: 28° C.
c. Culturing with or without agitation (liquid or solid)
5. Storing Condition
Temperature: −70° C.

Example 8

Sensory Evaluation of Isolated Microorganisms on Aluminum Fin (1) Culturing in Nutrient Medium For sensory evaluation of 11 species from among the microorganisms identified in Example 7, the microorganisms were cultured in nutrient media at 28° C. for 7 days. The procedure of culturing the bacteria in nutrient media was as follows.

① The isolated microorganisms were inoculated to a liquid nutrient medium.
② Culturing was performed at 28° C. for 5-7 days.
③ 100 µL of the bacteria cultured in the liquid medium were inoculated to a solid nutrient medium.
④ The inoculated bacteria were spread uniformly using a spreader.
⑤ The bacteria were cultured on a sealed Petri dish at 28° C. for 10 days.

(2) Sensory Evaluation on Aluminum Fin

A rectangular aluminum fin was sterilized and then dipped in a nutrient medium. For bacterial inoculation, culturing was performed in the nutrient medium under the same conditions of the steps ②-④. The sensory evaluation result is given in Table 8.

① Antimicrobial-treated aluminum fin: A commercially available, antimicrobial-coated evaporator core product was used.
② Non-antimicrobial-treated, hydrophilic-coated aluminum fin: An aluminum fin which was hydrophilic-coated only, without antimicrobial coating, was specially manufactured for comparison with the antibacterial-coated fin. Although the evaporator core was manufactured from aluminum to reduce weight, it can also be made from other metals such as copper, stainless steel, etc.

TABLE 8

| No. | Anti-microbial-treated fin | Non-anti-microbial-treated fin | Strain |
|---|---|---|---|
| 1 | odorless | odorless | *Methylobacterium aquaticum* HKMC-1 |
| 2 | odorless | odorless | *Methylobacterium brachiatum* HKMC-2 |
| 3 | odorless | odorless | *Methylobacterium platani* HKMC-3 |
| 4 | odorless | odorless | *Acinetobacter johnsonii* HKMC-4 |
| 5 | odorless | odorless | *Bacillus vietnamensis* HKMC-5 |
| 6 | odorless | odorless | *Brevibacillus invocatus* HKMC-6 |
| 7 | odorless | odorless | *Deinococcus ficus* HKMC-7 |
| 8 | odorless | odorless | *Leifsonia soli* HKMC-8 |
| 9 | odorless | odorless | *Pseudomonas nitroreducens* HKMC-9 |
| 10 | odorless | odorless | *Sphingomonas aquatilis* HKMC-10 |
| 11 | odorless | odorless | *Methylobacterium komagatae* HKMC-11 |

No odor was detectable for all of the 11 microorganism species when they were cultured after inoculation onto the antimicrobial-treated aluminum fin and the non-antimicrobial-treated fin.

Example 9

Evaluation of Optimal Condition For Coating Odorless Microorganisms (1) Analysis of Optimal Concentration For Coating Odorless Microorganisms on Fin For coating of the 11 odorless microorganism species on an evaporator core, optimal coating concentration for inoculating the microorganisms to a concentration of about $10^6$ CFU/g was investigated as described in the priority application of 2012. *Methylobacterium aquaticum* was cultured at 28° C. until the late log phase and then cultured at 4° C. for 18 hours after washing with sterilized 0.85% saline. After the culturing at 4° C., optical density (O.D.) was measured to be 0.749, 0.588, 0.55, 0.5 and 0.45. 2 g of a U-shaped fin was coated with the culture by dipping for 1 hour at room temperature and shaking at constant rpm. The fin coated with the microorganism at different concentrations was removed from the mixer and plated onto an R2A agar plate after serial dilution.

It was found out that the concentration of the microorganisms coated on the fin varied depending on the O.D. values. When O.D. was 0.749, the coating degree was about $1.53 \times 10^8 \pm 1.52 \times 10^7$ CFU/g fin. And, when O.D. was 0.588 and 0.55, the coating degree was about $4.00 \times 10^7 \pm 1.00 \times 10^7$ CFU/g fin and $1.03 \times 10^7 \pm 8.50 \times 10^5$ CFU/g fin, respectively. In addition, when O.D. was 0.5 and 0.45, the coating degree was $6.00 \times 10^6 \pm 7.00 \times 10^5$ CFU/g fin and $2.53 \times 10^6 \pm 3.51 \times 10^5$ CFU/g respectively. That is to say, the coating degree was proportional to O.D. The O.D. value of 0.5 at which the microorganisms were coated at a concentration of $10^6$ CFU/g, which is similar to the level of the evaporator core from which the microorganisms were isolated, was selected for coating of the other 10 odorless microorganism species.

(2) Evaluation of Coatability of Odorless Microorganisms on Evaporator Core and Fin As a result of a fin coating test, the 11 odorless microorganism species showed the same coating degree at the same O.D. regardless of the genus. Accordingly, the amount of *Methylobacterium aquaticum* coated on an evaporator core was measured using a culture corresponding to the O.D. value of the fin.

*Methylobacterium aquaticum* adjusted to O.D. 0.5 showed a coating degree of $8.95 \times 10^6 \pm 5.51 \times 10^5$ CFU/g fin on the evaporator core. When the same culture was coated on the evaporator core, the coating degree was $2.55 \times 10^6 \pm 3.51 \times 10^5$ CFU/g fin. Accordingly, it was confirmed that the microorganisms was coated with the same degree when the culture of the same O.D. is used.

Example 10

Sensory Evaluation of Isolated Microorganisms Coated on Evaporator Core (1) Coating of 11 Odorless Microorganism Species on Evaporator Core Coating and Sensory Evaluation For sensory evaluation of the microorganisms identified in Example 8, each of the 11 odorless microorganism species was coated on an evaporator core.

Offensive odors generated by the microorganisms were analyzed through an olfactory evaluation test. The microorganism-coated evaporator cores were evaluated by 15 sensory evaluation panels. As a result, the 11 microorganism species scored 1.78±0.41 (5-point scale, 0: no odor; 1: very weak odor (hardly detectable odor); 2: weak odor (difficult-to-distinguish odor); 3: distinct odor (distinguishable odor); 4: strong odor; 5: very strong odor). *Methylobacterium* sp. showed a lower-than-average score of 1.625±0.29. The 3 common strains, *Methylobacterium aquaticum*, *Methylobacterium brachiatum* and *Methylobacterium platani*, scored 1.6±0.35. *Deinococcus ficus* scored highest at 2.8, followed by *Bacillus vietnamensis* at 2.1 (Table 8).

Based on the sensory evaluation result, the 3 microorganism species which generate relatively strong odors, *Methylobacterium brachiatum*, *Bacillus vietnamensis* and *Deinococcus ficus*, were excluded.

TABLE 9

Sensory evaluation of microorganisms coated on evaporator core

| No. | Strain | Odor in air | Odor under reconstitution condition* | Evaluation result (5-point scale) | Selection |
|---|---|---|---|---|---|
| 1 | *Methylobacterium aquaticum* | odorless | odorless | 1.4 | selected |
| 2 | *Methylobacterium brachiatum* | odorless | X | 2 | — |
| 3 | *Methylobacterium platani* | odorless | odorless | 1.4 | selected |
| 4 | *Acinetobacter johnsonii* | odorless | odorless | 1.5 | selected |
| 5 | *Bacillus vietnamensis* | odorless | X | 2.1 | — |
| 6 | *Brevibacillus invocatus* | odorless | odorless | 1.5 | selected |
| 7 | *Deinococcus ficus* | odorless | X | 2.8 | — |
| 8 | *Leifsonia soli* | odorless | odorless | 1.7 | selected |

TABLE 9-continued

Sensory evaluation of microorganisms coated on evaporator core

| No. | Strain | Odor in air | Odor under reconstitution condition* | Evaluation result (5-point scale) | Selection |
|---|---|---|---|---|---|
| 9 | Pseudomonas nitroreducens | odorless | odorless | 1.6 | selected |
| 10 | Sphingomonas aquatilis | odorless | odorless | 1.6 | selected |
| 11 | Methylobacterium komagatae | odorless | odorless | 1.7 | selected |
| Ref. | Control (sterilized evaporator core) | — | — | 2.1 | |

Reconstitution condition*: Step 1: After supplying gasoline (nutritional source for microorganisms), a reconstitution apparatus was operated for 2 hours (temperature: 25° C., humidity: 50-90%, air velocity: 170 CMH, nutritional source: 10 ppm gasoline).
Step 2: After stopping the operation of the reconstitution apparatus (temperature: 25° C., humidity: 30-50%, air velocity: 0 CMH), odor was evaluated after slightly opening the inlet of the reconstitution apparatus.

(2) Sensory Evaluation of Combinations of Odorless Microorganisms

The 8 odorless microorganism species selected based on the sensory evaluation was combined with *Methylobacterium aquaticum* and *Methylobacterium platani* to obtain 14 optimized combinations of odorless microorganisms. For sensory evaluation of the combinations of odorless microorganisms, they were mixed with the same density and coated on an evaporator core.

As a result of olfactory evaluation, the average sensory evaluation score of the 14 combinations was 1.89±0.52 (5-point scale). The combination 14 which contained the common strains as well as *Acinetobacter johnsonii, Sphingomonas aquatilis* and *Pseudomonas nitroreducens* showed the lowest sensory evaluation score of 1.25 and the combination containing the common strains and *Acinetobacter johnsonii* showed the highest sensory evaluation score of 3.14 (Table 10). Based on this quantitative evaluation and an odor quality evaluation test, the 10 combinations excluding the 2 combinations containing the common strains and one of *Acinetobacter johnsonii* and *Brevibacillus invocatus*, the combination 7 containing *Brevibacillus invocatus, Sphingomonas aquatilis* and *Methylobacterium komagatae*, and the combination 13 containing *Leifsonia soli, Sphingomonas aquatilis* and *Pseudomonas nitroreducens* were selected for a final survival test.

TABLE 10

Sensory evaluation of combinations of odorless microorganisms

| No. | Combination | Olfactory evaluation | Result |
|---|---|---|---|
| 1 | Common strains (*Methylobacterium aquaticum* and *Methylobacterium platani*) | 1.98 | selected |
| 2 | *Acinetobacter johnsonii* | 3.14 | X |
| 3 | *Brevibacillus invocatus* | 2.12 | X |
| 4 | *Sphingomonas aquatilis* and *Brevibacillus invocatus* | 1.38 | selected |
| 5 | *Leifsonia soli* and *Methylobacterium komagatae* | 1.38 | selected |
| 6 | *Acinetobacter johnsonii, Sphingomonas aquatilis* and *Methylobacterium komagatae* | 1.33 | selected |
| 7 | *Brevibacillus invocatus, Sphingomonas aquatilis* and *Methylobacterium komagatae* | 2.33 | X |
| 8 | *Pseudomonas nitroreducens* | 2.13 | selected |
| 9 | *Acinetobacter johnsonii* and *Pseudomonas nitroreducens* | 2 | selected |
| 10 | *Brevibacillus invocatus, Acinetobacter johnsonii* and *Pseudomonas nitroreducens* | 1.5 | selected |
| 11 | *Leifsonia soli* and *Pseudomonas nitroreducens* | 1.86 | selected |
| 12 | *Brevibacillus invocatus, Sphingomonas aquatilis* and *Pseudomonas nitroreducens* | 1.7 | selected |
| 13 | *Leifsonia soli, Sphingomonas aquatilis* and *Pseudomonas nitroreducens* | 2.38 | X |
| 14 | *Acinetobacter johnsonii, Sphingomonas aquatilis* and *Pseudomonas nitroreducens* | 1.25 | selected |

Example 11

Survival Evaluation of 10 Combinations For 30 Days

For the combinations of microorganisms selected based on the result of sensory evaluation in Example 9-(2), survival evaluation was conducted for 30 days. The number and microorganisms of the combinations are as follows (Table 11).

TABLE 11

Combinations of microorganisms used in survival evaluation for 30 days

| No. | Combination |
|---|---|
| 1 | *Methylobacterium aquaticum, Methylobacterium platani, Brevibacillus invocatus, Sphingomonas aquatilis* and *Pseudomonas nitroreducens* |
| 2 | *Methylobacterium aquaticum, Methylobacterium platani, Acinetobacter johnsonii, Sphingomonas aquatilis* and *Pseudomonas nitroreducens* |
| 3 | *Methylobacterium aquaticum, Methylobacterium platani, Acinetobacter johnsonii, Sphingomonas aquatilis* and *Methylobacterium komagatae* |
| 4 | *Methylobacterium aquaticum, Methylobacterium platani, Brevibacillus invocatus, Acinetobacter johnsonii* and *Pseudomonas nitroreducens* |
| 5 | *Methylobacterium aquaticum, Methylobacterium platani, Acinetobacter johnsonii* and *Pseudomonas nitroreducens* |
| 6 | *Methylobacterium aquaticum, Methylobacterium platani, Leifsonia soli* and *Pseudomonas nitroreducens* |

TABLE 11-continued Combinations of microorganisms used in survival evaluation for 30 days

| No. | Combination |
|---|---|
| 7 | *Methylobacterium aquaticum, Methylobacterium platani, Leifsonia soli* and *Methylobacterium komagatae* |
| 8 | *Methylobacterium aquaticum, Methylobacterium platani, Sphingomonas aquatilis* and *Brevibacillus invocatus* |
| 9 | *Methylobacterium aquaticum, Methylobacterium platani* and *Pseudomonas nitroreducens* |
| 10 | *Methylobacterium aquaticum* and *Methylobacterium platani* |

The microorganisms were cultured and coated on an evaporator core in order from the combination 1 to the combination 10. The coating degree was $10^6$ CFU/g fin.

Figure 2:
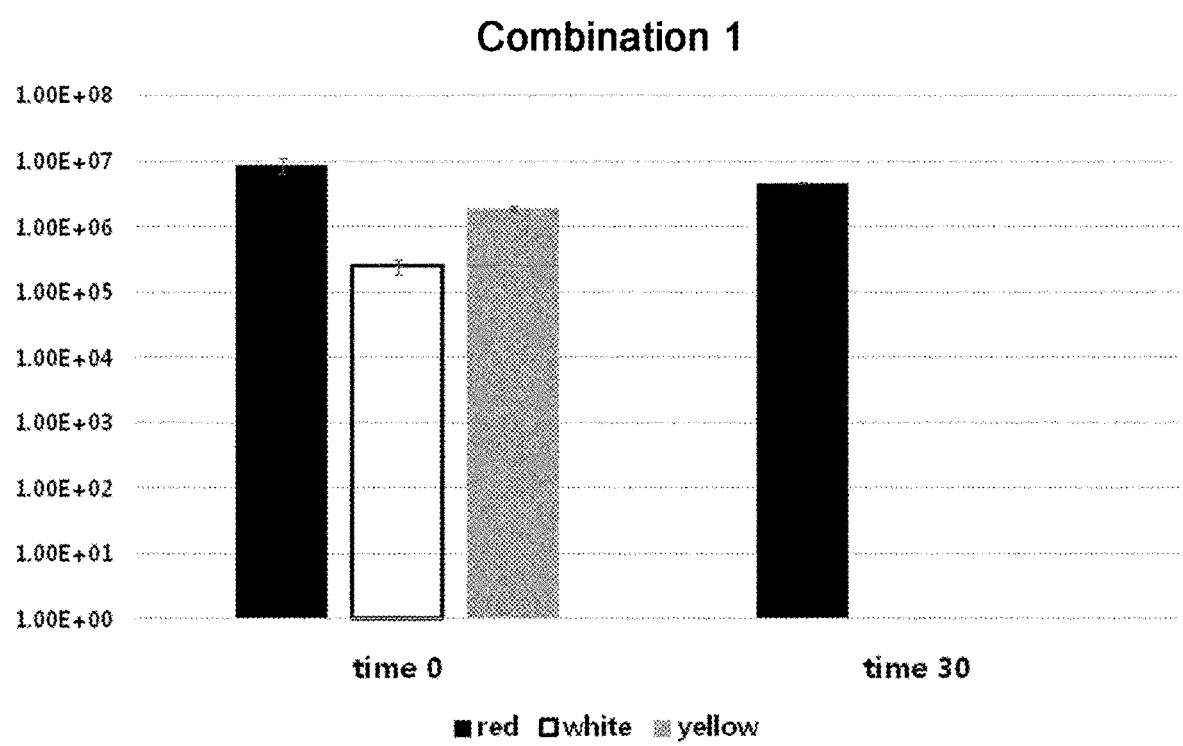
FIG. 2 shows the population of colonies of different colors for a combination 1 in survival evaluation for 30 days.
Figure 3:
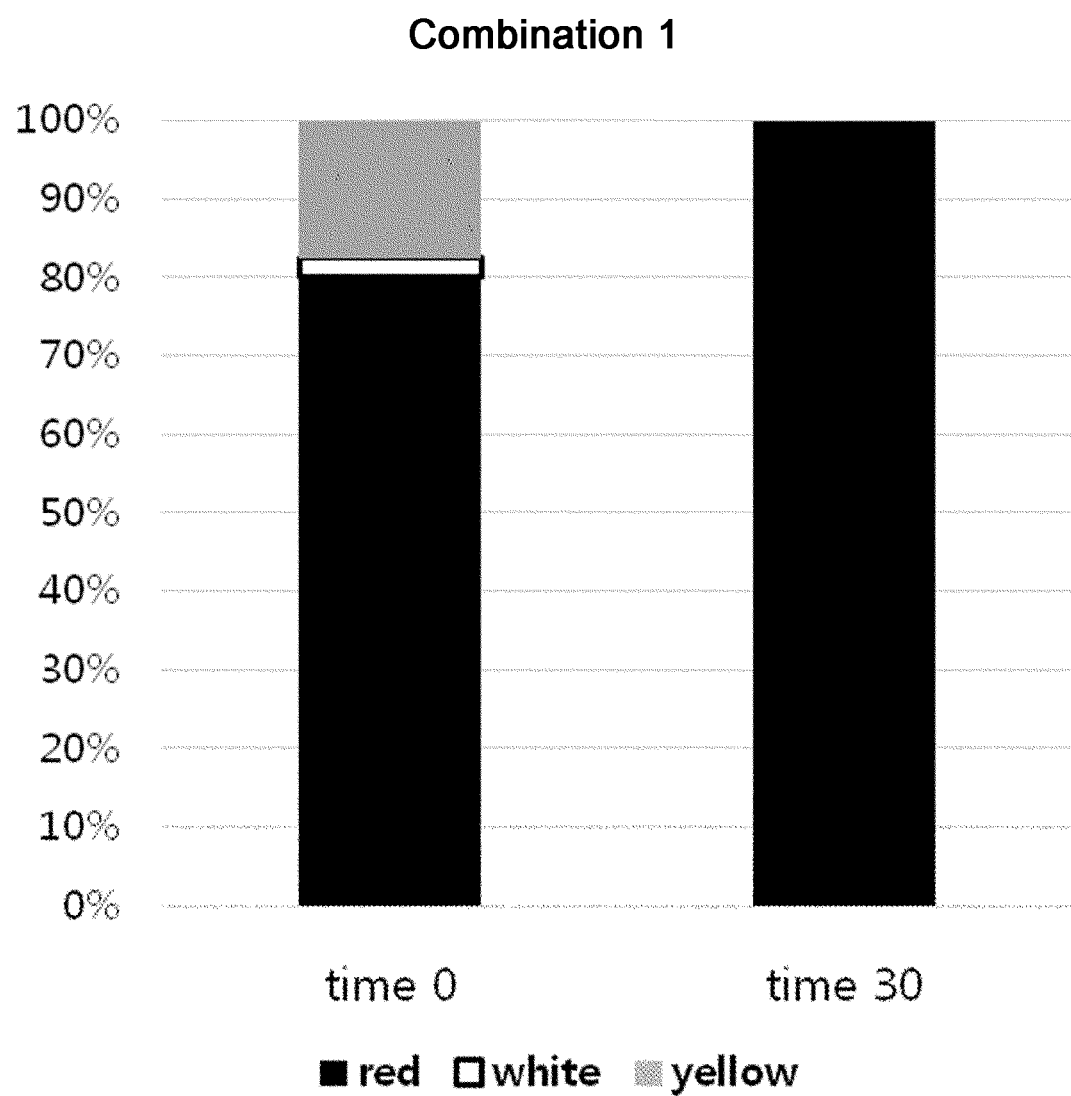
FIG. 3 shows the ratio of colonies of different colors for a combination 1 in survival evaluation for 30 days.
Figure 4:
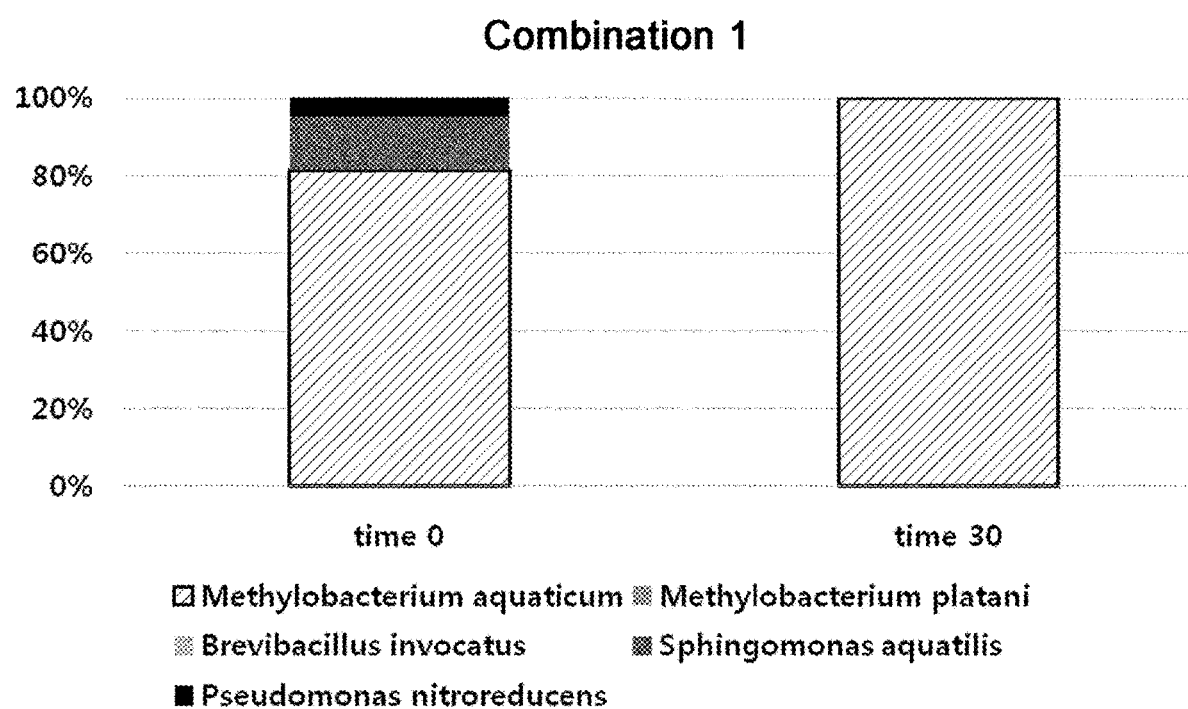
FIG. 4 shows the ratio of strains for a combination 1 in survival evaluation for 30 days measured by REP-PCR.

The combination 1 showed a coating degree of $1.09 \times 10^7 \pm 8.65 \times 10^5$ CFU/g fin on the evaporator core. A red colony was detected at $8.70 \times 10^6 \pm 2.35 \times 10^6$ CFU/g fin, a white colony at $2.50 \times 10^5 \pm 7.07 \times 10^4$ CFU/g fin, and a yellow colony at $1.90 \times 10^6 \pm 1.73 \times 10^5$ CFU/g fin. 30 days later, the total bacterial count was $4.63 \times 10^5 \pm 5.09 \times 10^4$ CFU/g fin, with that of the red colony only being $4.63 \times 10^6 \pm 1.53 \times 10^5$ CFU/g fin (FIG. 2). That is to say, the proportion of the red colony, which had accounted for over 80%, was increased to 100% 30 days later (FIG. 3). Based on the phenotype, the red colony was suspected to contain *Methylobacterium* which contains a pink pigment. Upon REP-PCR analysis, *Methylobacterium platani* and *Brevibacillus invocatus* were not detected at time 0. Particularly, it is to be noted that the *Methylobacterium platani* that was used as a common strain was not detected. For the combination 1, *Methylobacterium aquaticum* was detected the most in 70 out of a total of 86 REP-PCR samples at time 0. *Sphingomonas aquatilis* was detected in 12 samples, and *Pseudomonas nitroreducens* was detected in 4 samples. After 30 days, *Methylobacterium aquaticum* was detected in all the 32 samples, whereas the other microorganisms were not detected (FIG. 4).

Figure 5:
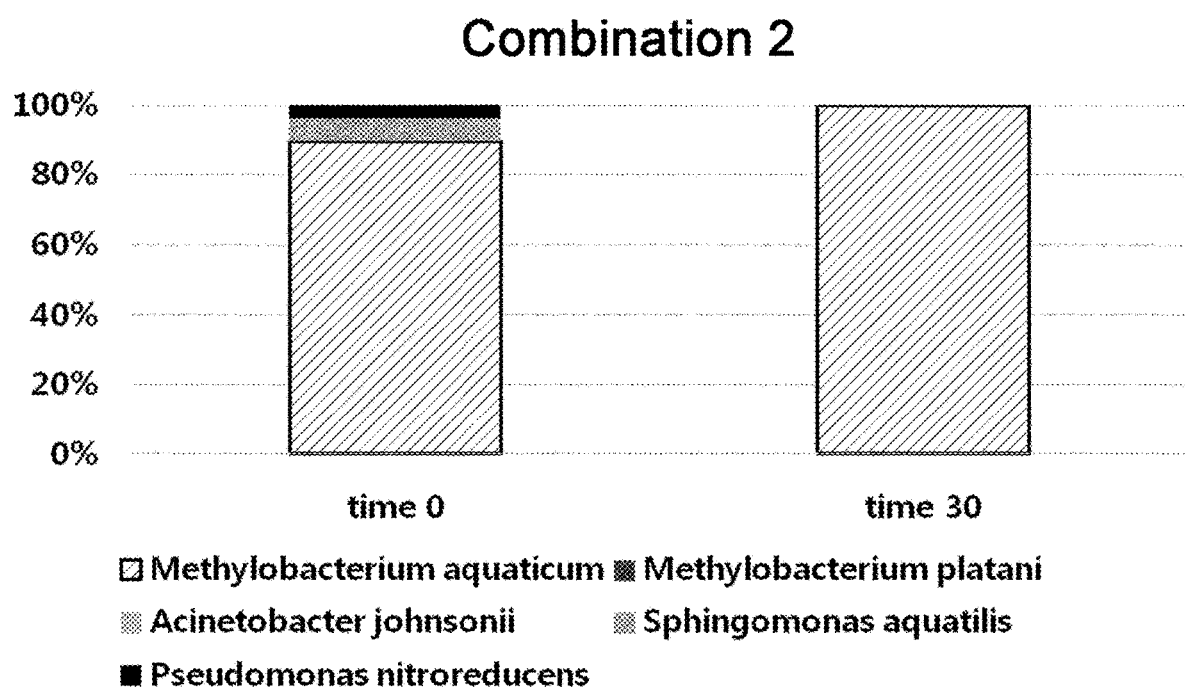
FIG. 5 shows the ratio of strains for a combination 2 in survival evaluation for 30 days measured by REP-PCR.

In the combination 2, *Acinetobacter johnsonii, Sphingomonas aquatilis* and *Pseudomonas nitroreducens* were used together with the common strains *Methylobacterium aquaticum* and *Methylobacterium platani*. At time 0, the total bacterial count on the evaporator core was $1.52 \times 10^7 \pm 5.42 \times 10^5$ CFU/g fin. 30 days later, the total bacterial count on the evaporator core was $3.23 \times 10^6 \pm 8.39 \times 10^4$ CFU/g fin. REP-PCR pattern analysis revealed that *Methylobacterium aquaticum, Sphingomonas aquatilis* and *Pseudomonas nitroreducens* were surviving on the evaporator core at time 0. Out of 105 REP-PCR samples, *Methylobacterium aquaticum* was detected in 94 samples, *Sphingomonas aquatilis* was detected in 7 samples, and *Pseudomonas nitroreducens* was detected in 4 samples. After 30 days, *Methylobacterium aquaticum* was detected in all the 30 REP-PCR samples (FIG. 5).

Figure 6:
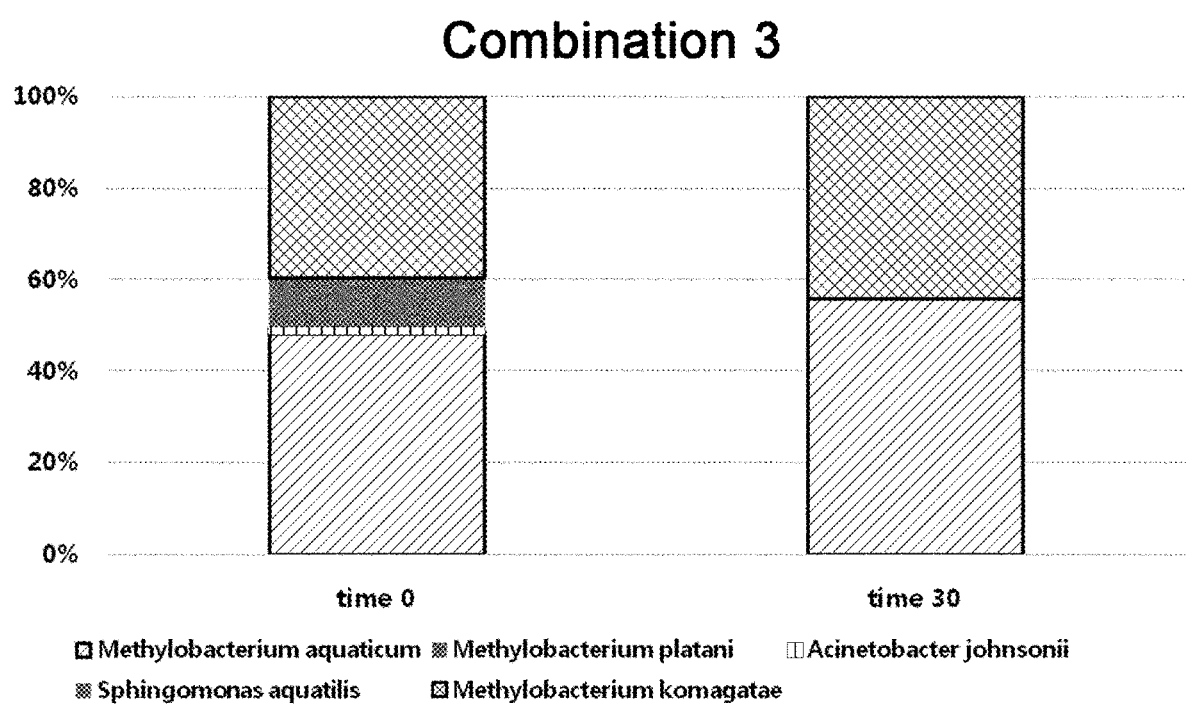
FIG. 6 shows the ratio of strains for a combination 3 in survival evaluation for 30 days measured by REP-PCR.
Figure 7:
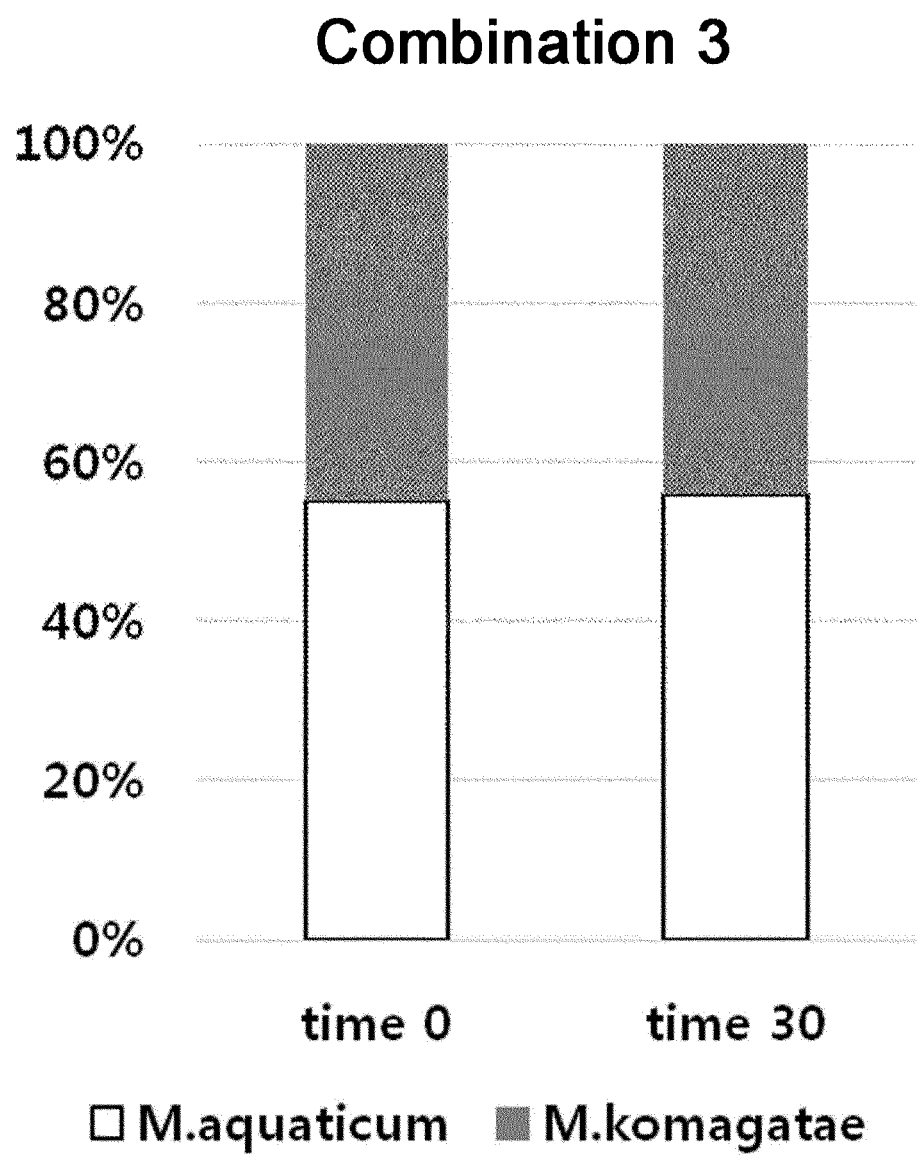
FIG. 7 shows the ratio of *Methylobacterium* sp. strains for a combination 3 in survival evaluation for 30 days measured by REP-PCR.

For the combination 3, the total bacterial count was $1.83 \times 10^7 \pm 3.89 \times 10^5$ CFU/g fin at time 0. 30 days later, total bacterial count was $5.23 \times 10^6 \pm 1.50 \times 10^5$ CFU/g fin. When the population of microorganisms was analyzed by REP-PCR, among the 5 microorganisms contained in the combination, 4 microorganisms *Methylobacterium aquaticum, Acinetobacter johnsonii, Sphingomonas aquatilis* and *Methylobacterium komagatae* excluding *Methylobacterium platani* were surviving on the evaporator core at time 0. After 30 days, *Methylobacterium komagatae* as well as *Methylobacterium aquaticum*, one of the common strains, was surviving. At time 0, out of 101 samples, *Methylobacterium aquaticum* was detected in 49 samples, *Acinetobacter johnsonii* was detected in 1 sample, *Sphingomonas aquatilis* was detected in 11 samples, and *Methylobacterium komagatae* was detected in 40 samples. After 30 days, *Methylobacterium aquaticum* was detected in 19 samples and *Methylobacterium komagatae* was detected in 15 samples (FIG. 6). It was found that the ratio of the surviving two *Methylobacterium* species was constant at about 1:1 for 30 days (FIG. 7).

Figure 8:
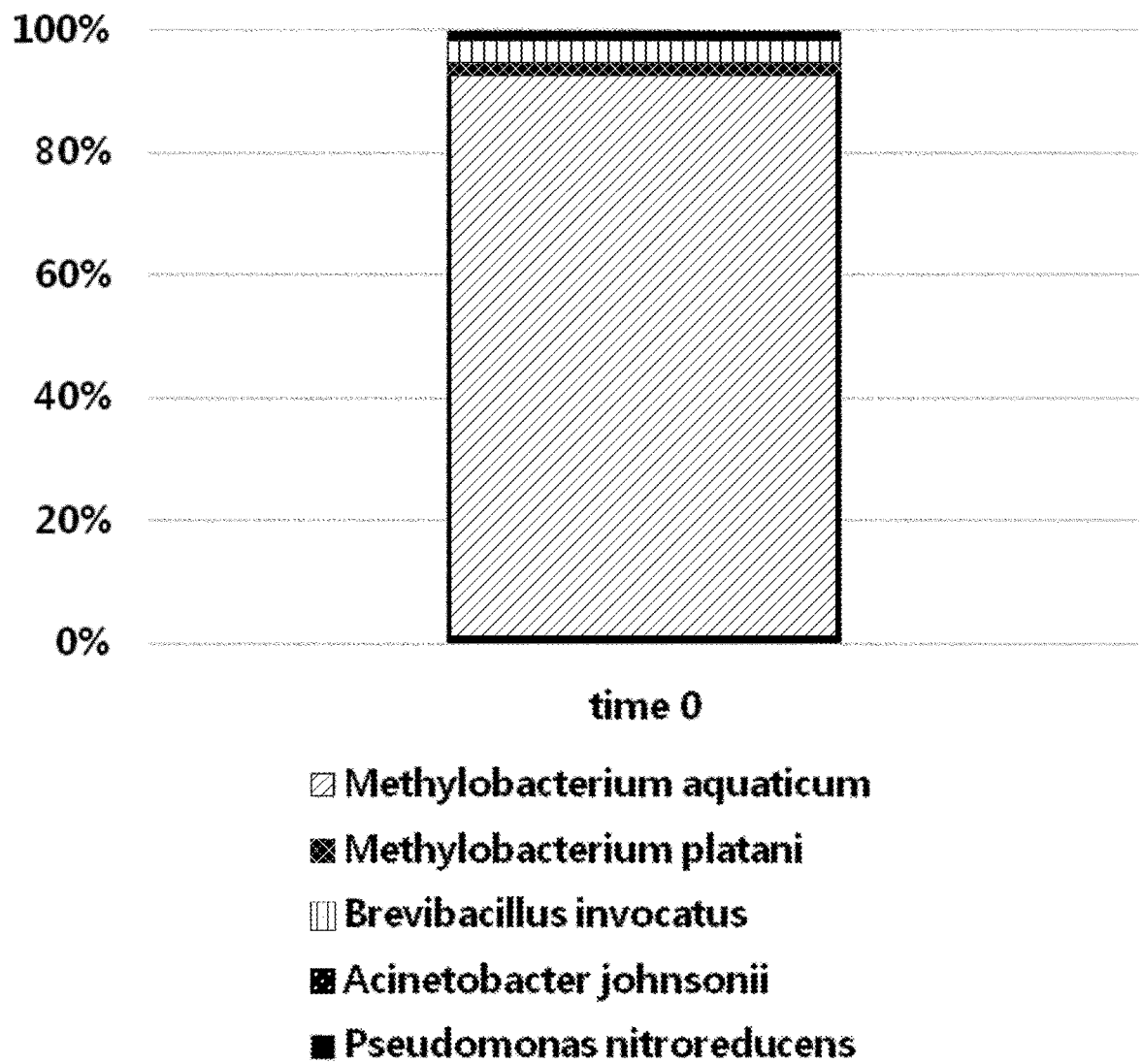
FIG. 8 shows the ratio of strains for a combination 4 in survival evaluation for 30 days measured by REP-PCR.

For the combination 4, the total bacterial count of the 5 strains was $2.04 \times 10^7 \pm 4.91 \times 10^5$ CFU/g fin at the time of coating. When the population of microorganisms was analyzed by REP-PCR, out of 86 samples, *Methylobacterium aquaticum* was detected in 80 samples, *Methylobacterium platani* was detected in 1 sample, *Brevibacillus invocatus* was detected in 3 samples, and *Pseudomonas nitroreducens* was detected in 2 samples (FIG. 8).

Figure 9:
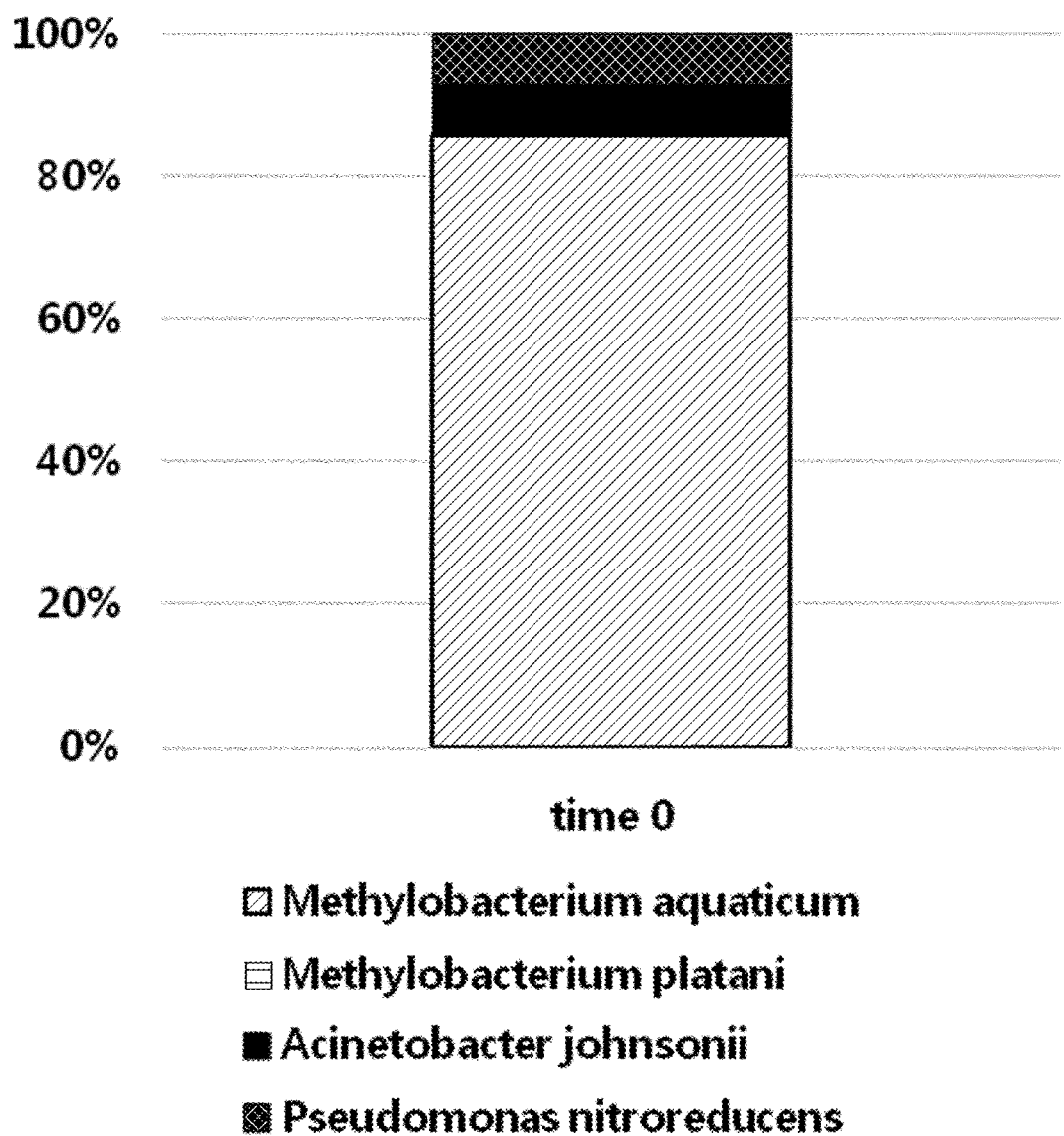
FIG. 9 shows the ratio of strains for a combination 5 in survival evaluation for 30 days measured by REP-PCR.

The combination 5 consisted of 4 strains *Methylobacterium aquaticum, Methylobacterium platani, Acinetobacter johnsonii* and *Pseudomonas nitroreducens*. At the time of coating on an evaporator core, the total bacterial count was $2.86 \times 10^7 \pm 1.19 \times 10^6$ CFU/g fin. When the population of microorganisms was analyzed by REP-PCR, out of 28 samples, *Methylobacterium aquaticum* was detected in 24 samples, and *Acinetobacter johnsonii* and *Pseudomonas nitroreducens* were detected in 2 samples, respectively (FIG. 9).

From the survival evaluation of the combinations of microorganisms, it was found out that the *Methylobacterium platani* used as the common strain show low survivability when coated on the evaporator core with other microorganisms. Therefore, additional microorganism combinations were prepared using the other common strain *Methylobacterium aquaticum* and the *Methylobacterium komagatae*, which showed comparable survivability for 30 days, and survivability was evaluated for 30 days.

Example 12

Survival Evaluation of Additional 6 Combinations For 30 Days

*Methylobacterium komagatae* was selected as a microorganism to replace *Methylobacterium platani*, which showed poor survivability in the survival evaluation for 30 days. *Methylobacterium komagatae* was combined with the common strain *Methylobacterium aquaticum* to prepare 6 additional combinations of microorganisms (Table 12). The additionally prepared combinations contained a small number of microorganisms that exhibited excellent survivability, although they were not odorless, in order to prepare more stable combinations.

TABLE 12

Additional combinations of microorganisms used in survival evaluation for 30 days Combination A  *Methylobacterium aquaticum, Methylobacterium komagatae, Bacillus vietnamensis* and *Deinococcus ficus*
B  *Methylobacterium aquaticum, Methylobacterium komagatae, Curtobacterium flaccumfaciens, Deinococcus apachensis* and *Bacillus subtilis* subsp. *Subtilis*
C  *Methylobacterium aquaticum, Methylobacterium komagatae, Spirosoma linguale, Sphingomonas dokdonensis* and *Leifsonia soli*
D  *Methylobacterium aquaticum, Methylobacterium komagatae, Microbacterium flavescens, Leifsonia shinshuensis* and *Methylobacterium aerolatum*
E  *Methylobacterium aquaticum, Methylobacterium komagatae, Spirosoma panaciterrae, Flavobacterium oceanosedimentum* and *Brevundimonas kwangchunensis*
F  *Methylobacterium aquaticum, Methylobacterium komagatae, Methylobacterium brachiatum, Paenibacillus timonensis* and *Rhizobium massiliae, Bacillus lichemformis*

Figure 10:
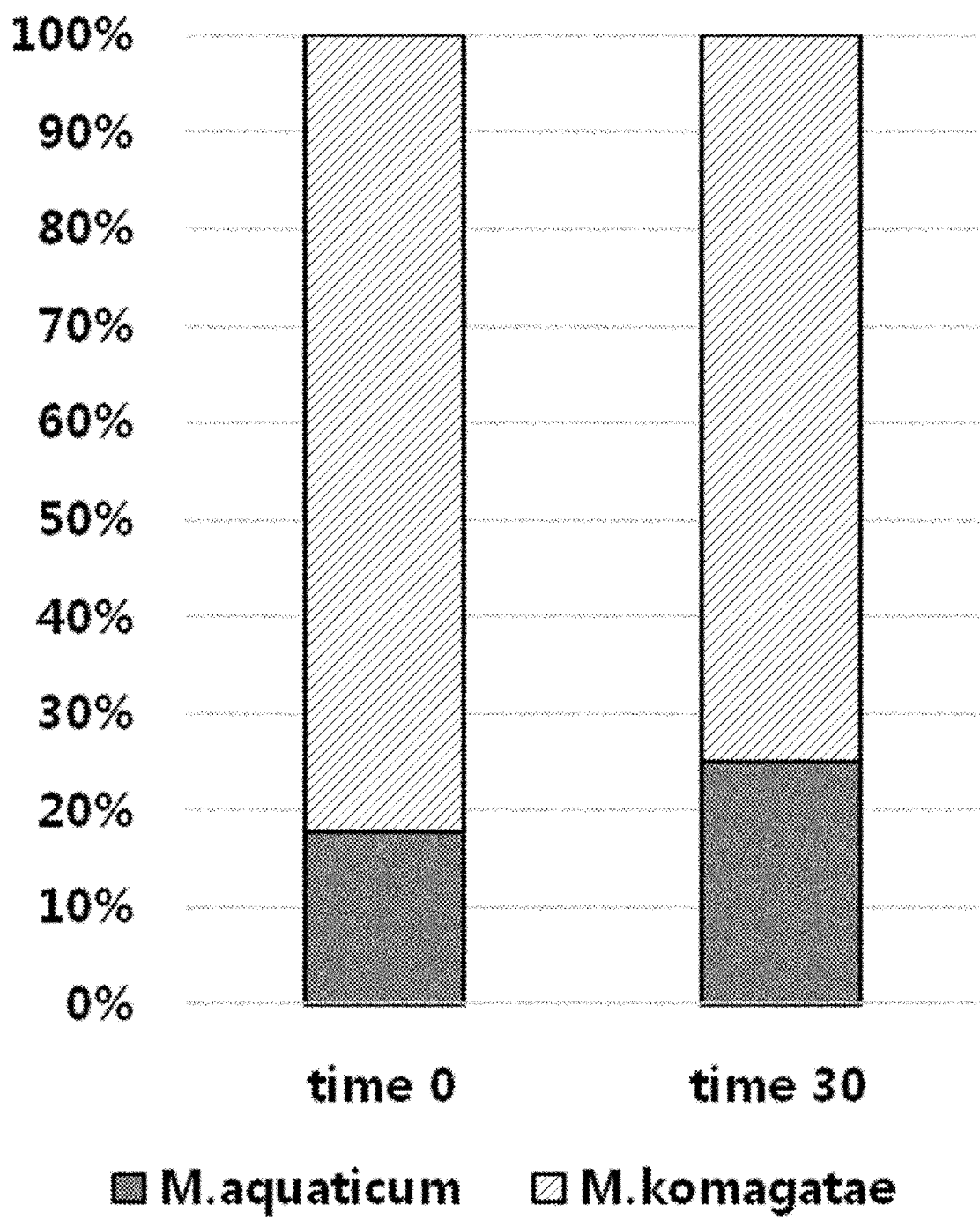
FIG. 10 shows the ratio of strains for a combination A in survival evaluation for 30 days measured by REP-PCR.

For the combination A, the total bacterial count on the evaporator core was $4.30\times10^6\pm1.25\times10^6$ CFU/g fin at the time of coating. Even after 30 days, the microorganisms were surviving at $4.30\times10^6\pm1.25\times10^6$ CFU/g fin. When the population of the coated microorganisms was investigated by REP-PCR pattern analysis, out of 45 samples, *Methylobacterium aquaticum* was detected in 8 samples and *Methylobacterium komagatae* was detected in 37 samples. After 30 days, out of 20 samples, *Methylobacterium aquaticum* was detected in 5 samples, *Methylobacterium komagatae* was detected in 15 samples. Although the ratio of *Methylobacterium aquaticum* was slightly increased, the change was not significant (FIG. 10).

Figure 11:
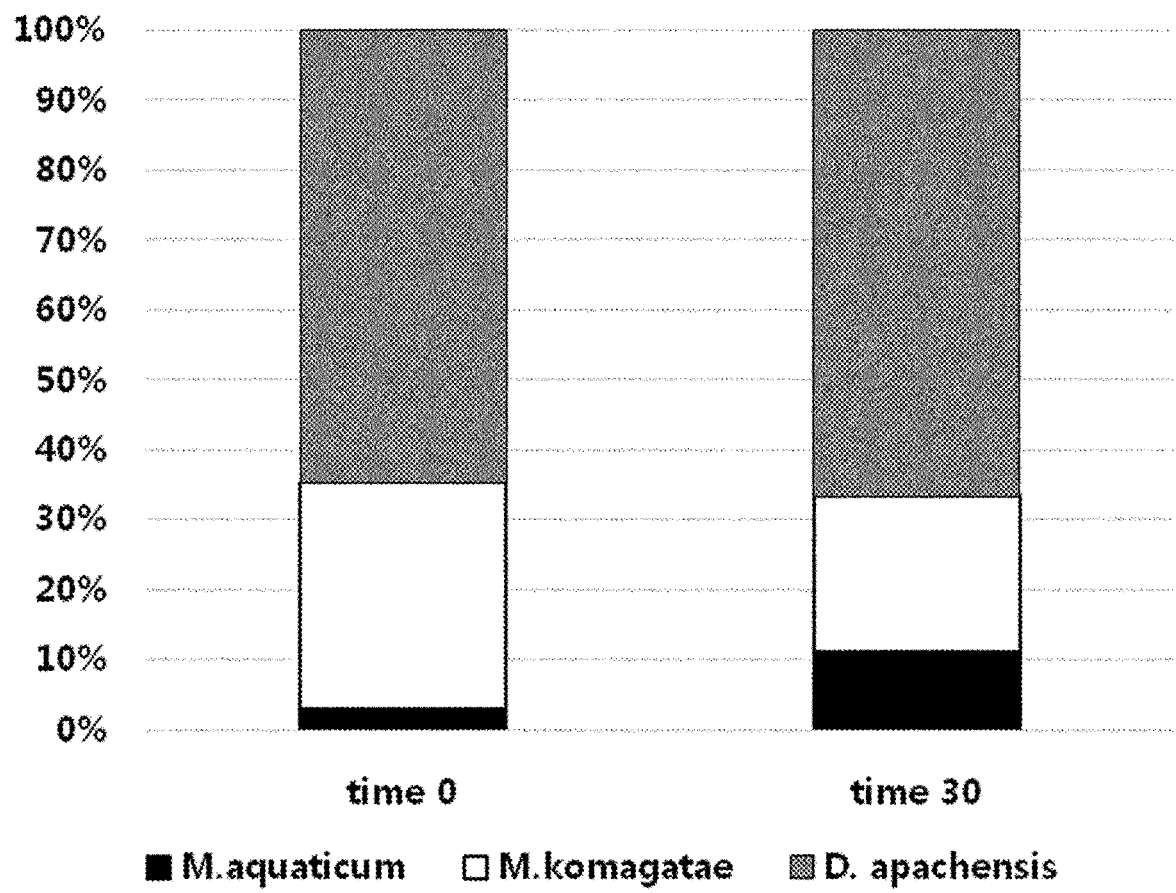
FIG. 11 shows the ratio of strains for a combination B in survival evaluation for 30 days measured by REP-PCR.

For the combination B, the total bacterial count was $2.07\times10^7\pm1.11\times10^6$ CFU/g fin at time 0. After 30 days, the total bacterial count was $1.74\times10^7\pm1.30\times10^6$ CFU/g fin. When the population of the microorganisms was investigated by REP-PCR, out of 34 representative samples, *Methylobacterium aquaticum* was detected in 1 sample and *Methylobacterium komagatae* was detected in 11 samples. All of the other 22 samples were found to be *Deinococcus apachensis*. That is to say, 40% or more of the coated microorganisms was *Deinococcus apachensis* (FIG. 11). After 30 days, REP-PCR pattern analysis revealed that the surviving microorganisms were *Methylobacterium aquaticum* 11.1%, *Methylobacterium komagatae* 22.2% and *Deinococcus apachensis* 66.6%. That is to say, although the ratio of *Methylobacterium aquaticum* was slightly increased as compared to time 0, all of the 3 microorganisms were surviving.

For the combination C, *Methylobacterium aquaticum, Methylobacterium komagatae, Spirosoma linguale, Sphingomonas dokdonensis* and *Leifsonia soli* were used. When the combination of the 5 strains was coated on an evaporator core, the total bacterial count was $7.53\times10^6\pm3.74\times10^5$ CFU/g fin. After 30 days, the total bacterial count was $3.70\times10^6\pm1.37\times10^5$ CFU/g fin.

Figure 12:
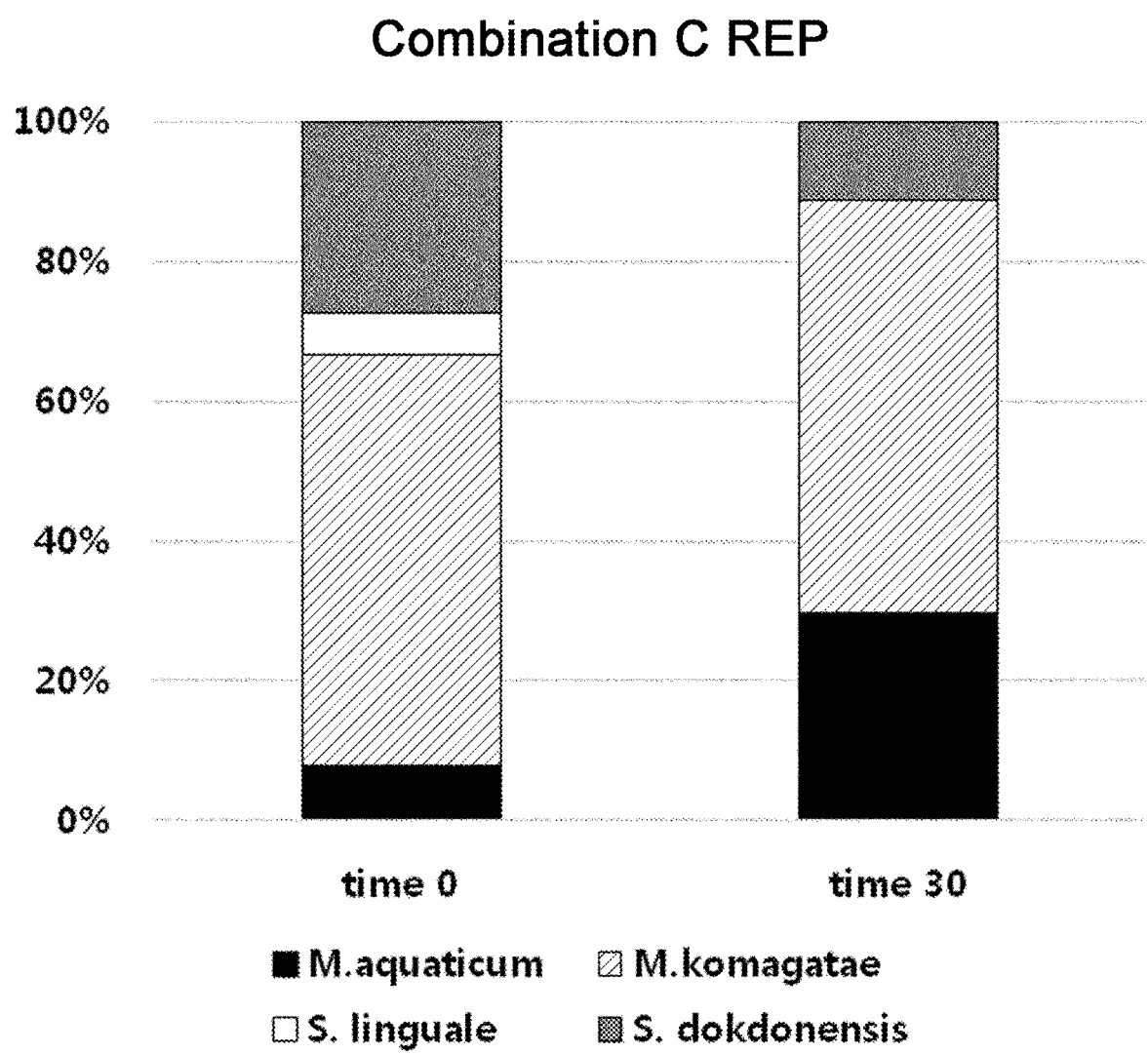
FIG. 12 shows the ratio of strains for a combination C in survival evaluation for 30 days measured by REP-PCR.

As a result of REP-PCR pattern analysis for identification of the surviving microorganisms, out of 51 representative samples, *Methylobacterium aquaticum* was detected in 4 samples, *Methylobacterium komagatae* was detected in 30 samples, *Spirosoma linguale* was detected in 3 samples and *Sphingomonas dokdonensis* was detected in 14 samples at time 0. After 30 days, *Methylobacterium aquaticum* was 29.6% and *Methylobacterium komagatae* was 59.2%. That is to say, the ratio of *Methylobacterium aquaticum* was slightly increased. *Spirosoma linguale* was not detected and the ratio of *Sphingomonas dokdonensis* was slightly decreased to 11.1% as compared to time 0 (FIG. 12).

Figure 13:
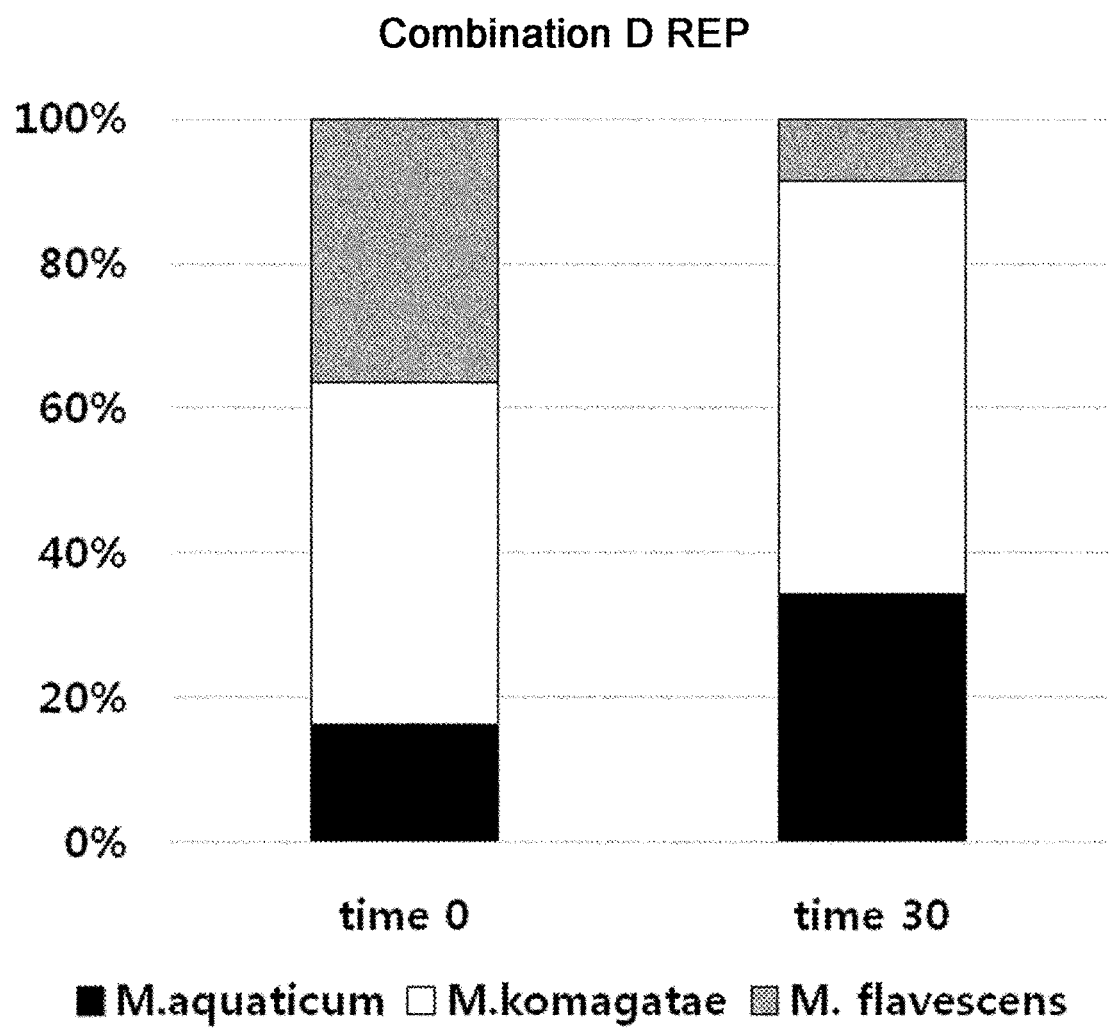
FIG. 13 shows the ratio of strains for a combination D in survival evaluation for 30 days measured by REP-PCR.

For the combination D, the total bacterial count at time 0 was $1.75\times10^7\pm1.24\times10^6$ CFU/g fin. After 30 days, the total bacterial count was $6.03\times10^6\pm1.01\times10^6$ CFU/g fin. When the ratio of the bacteria was investigated by REP-PCR, *Methylobacterium aquaticum* was 16.3%, *Methylobacterium komagatae* was 47.3% and *Microbacterium flavescens* was 36.4% at time 0. After 30 days, *Methylobacterium aquaticum* was increased to 34.3% and *Methylobacterium komagatae* was also increased slightly to 57.1%. In contrast, *Microbacterium flavescens* was decreased to 8.6% (FIG. 13).

Figure 14:
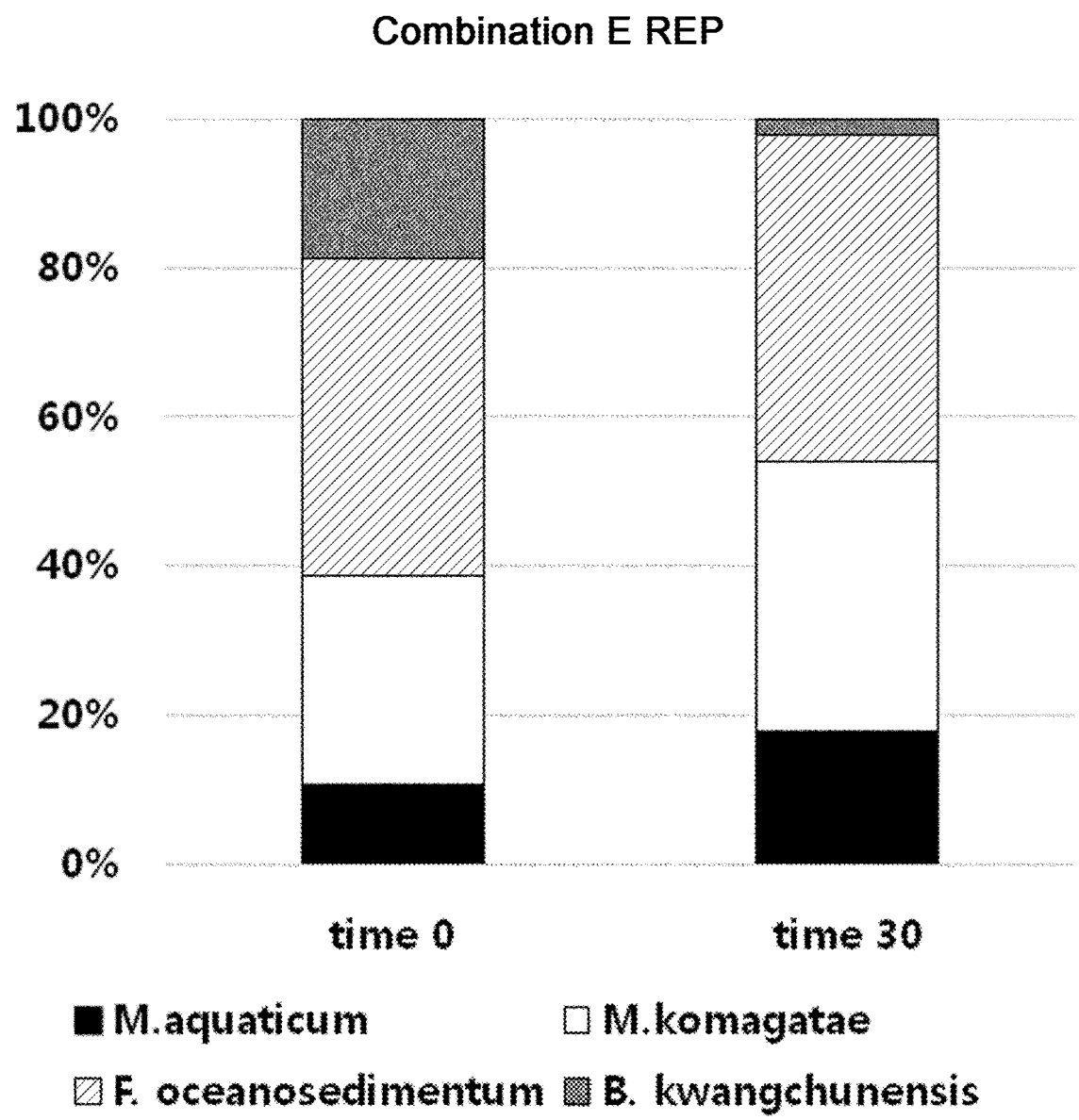
FIG. 14 shows the ratio of strains for a combination E in survival evaluation for 30 days measured by REP-PCR.

For the combination E, the total bacterial count was $8.53\times10^6\pm3.21\times10^5$ CFU/g fin at time 0. After 30 days, the total bacterial count was $1.20\times10^6\pm3.84\times10^4$ CFU/g fin. When population was analyzed by REP-PCR, out of 75 samples, *Methylobacterium aquaticum* was detected in 8 samples, *Methylobacterium komagatae* was detected in 21 samples, *Flavobacterium oceanosedimentum* was detected in 32 samples and *Brevundimonas kwangchunensis* was detected in 14 samples at time 0. After 30 days, out of 89 representative samples, *Methylobacterium aquaticum* was detected in 16 samples, *Methylobacterium komagatae* was detected in 32 samples, *Flavobacterium oceanosedimentum* was detected in 39 samples and *Brevundimonas kwangchunensis* was detected in 2 samples, respectively (FIG. 14). *Spirosoma panaciterrae* was hardly detectable at time 0 and the ratio of *Brevundimonas kwangchunensis* was significantly decreased after 30 days.

Figure 15:
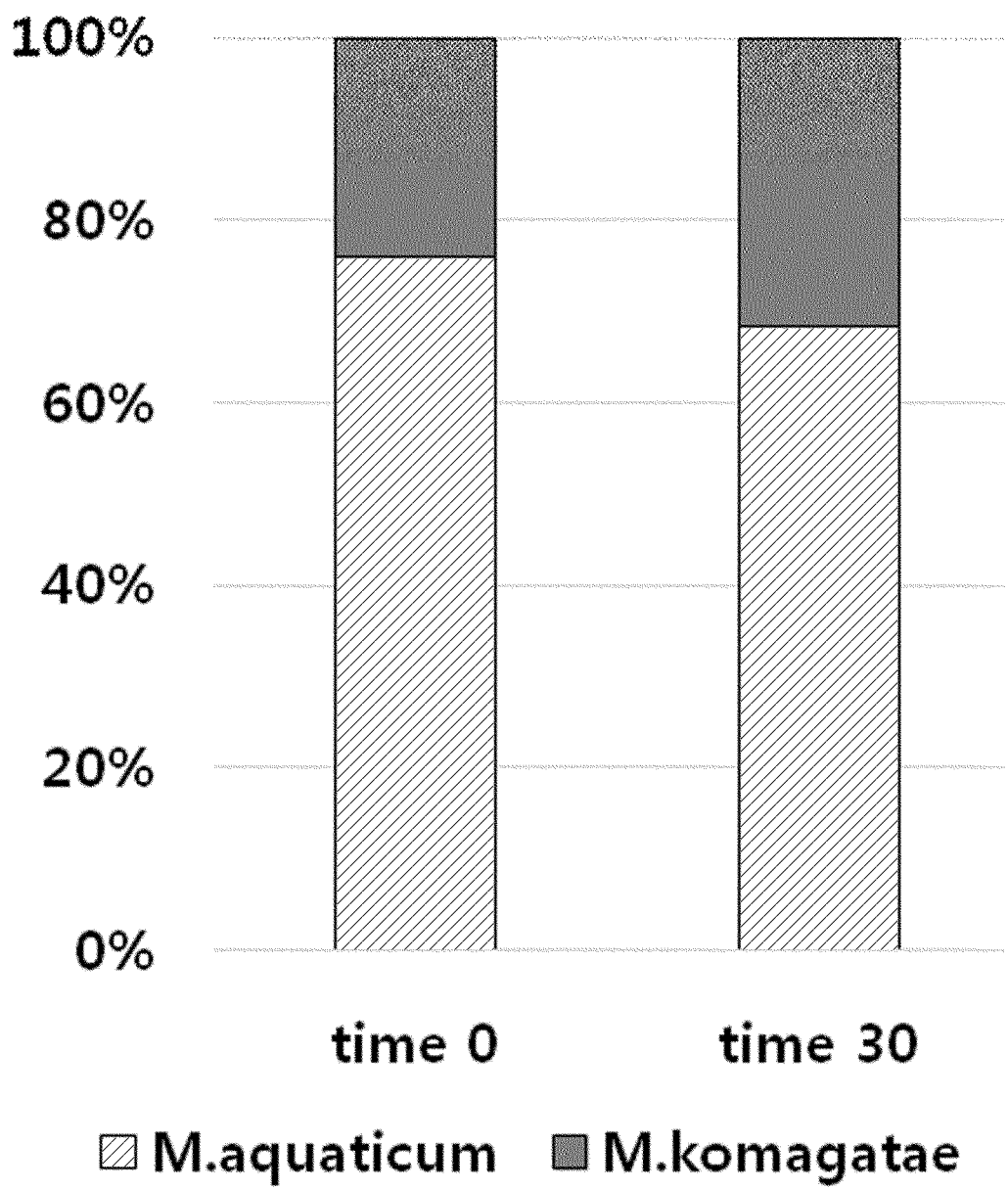
FIG. 15 shows the ratio of strains for a combination F in survival evaluation for 30 days measured by REP-PCR.

For the combination F, 6 strains including the two *Methylobacterium* sp. common strains were used. At time 0, the total bacterial count was $1.60\times10^7\pm1.15\times10^6$ CFU/g fin. After 30 days, the total bacterial count was $9.03\times10^6\pm2.42\times10^5$ CFU/g fin. When the population of the strains was analyzed by REP-PCR, out of 71 representative samples, *Methylobacterium aquaticum* was detected in 54 samples and *Methylobacterium komagatae* was detected in 17 samples at time 0. After 30 days, *Methylobacterium aquaticum* was detected in 50 samples and *Methylobacterium komagatae* was detected in 23 samples out of 73 samples (FIG. 15).

Example 13

Survival Evaluation of Combinations of Common Strains For 90 Days

For evaluation of long-term effect for 90 days, various combinations of odorless microorganisms were prepared.

First, *Methylobacterium aquaticum* and *Methylobacterium komagatae*, as common strains included in all combinations, were tested for 90 days.

Figure 16:
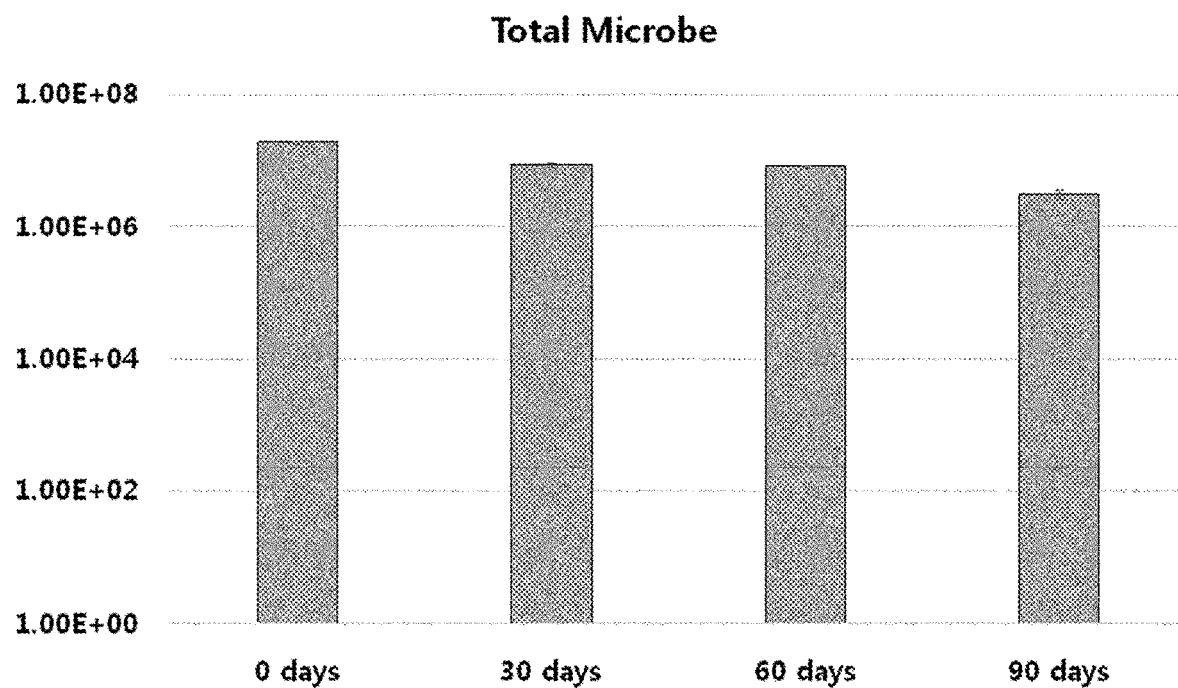
FIG. 16 shows the population of a combination of *Methylobacterium aquaticum* and *Methylobacterium komagatae* in survival evaluation for 90 days.
Figure 17:
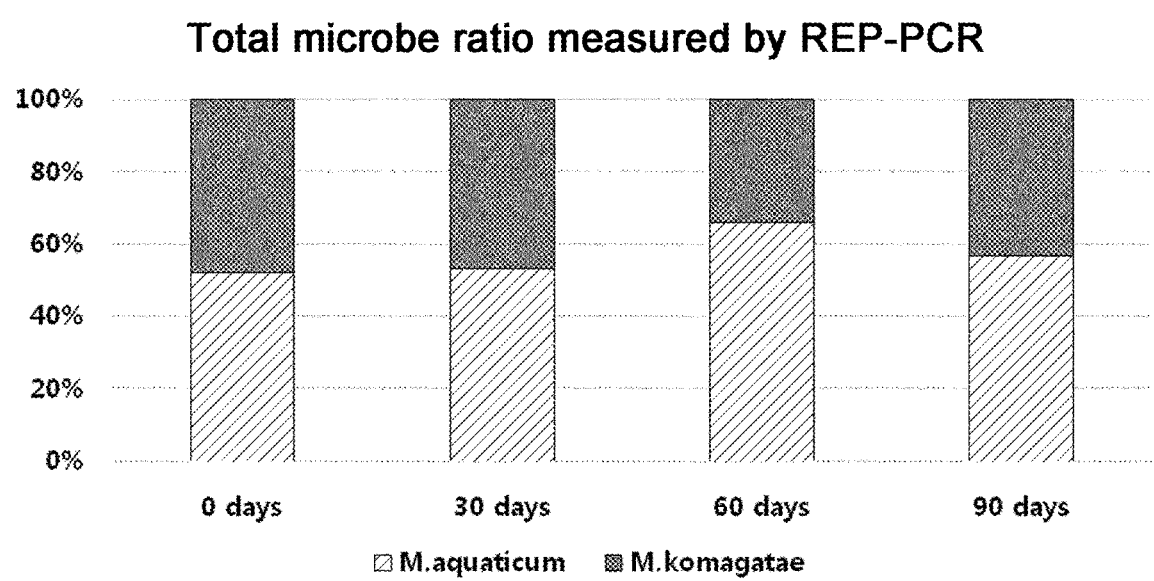
FIG. 17 shows the ratio of strains for a combination of *Methylobacterium aquaticum* and *Methylobacterium komagatae* in survival evaluation for 90 days measured by REP-PCR.

When the two *Methylobacterium* sp. strains were coated on an evaporator core, the total bacterial count was measured to be $1.92 \times 10^7 \pm 8.02 \times 10^5$ CFU/g fin at time 0. 5 g of the fin was taken every 30 days and the total bacterial count was measured. The number of surviving bacterial was $8.70 \times 10^6 \pm 6.56 \times 10^5$ CFU/g fin after 30 days, $4.10 \times 10^6 \pm 3.00 \times 10^5$ CFU/g fin after 60 days and $3.13 \times 10^6 \pm 5.51 \times 10^5$ CFU/g fin after 90 days (FIG. 16). 71, 66, 41 and 44 representative samples taken from each sampling location were subjected to REP-PCR pattern analysis. At time 0, *Methylobacterium aquaticum* was detected in 37 samples and *Methylobacterium komagatae* was detected in 34 samples. After 30, 60 and 90 days, the numbers of the samples were 35 and 31, 27 and 14, and 25 and 19, respectively (FIG. 17). That is to say, the % ratio of *Methylobacterium aquaticum* was 52.1-65.8% and that of *Methylobacterium komagatae* was 34.1-47.9%. This uniform ratio suggests that the two strains can coexist for a long-term period.

Example 14

Survival Evaluation of Combinations of Common Strains on Vehicle Jig

In order to investigate the growth of a combination of the common strains *Methylobacterium aquaticum* and *Methylobacterium komagatae* under an outdoor condition, the two strains were coated on an evaporator core and the evaporator core was mounted on a jig which was in turn installed on a vehicle roof. After operation, the change in the strains exposed to outdoor air was investigated.

Figure 18:
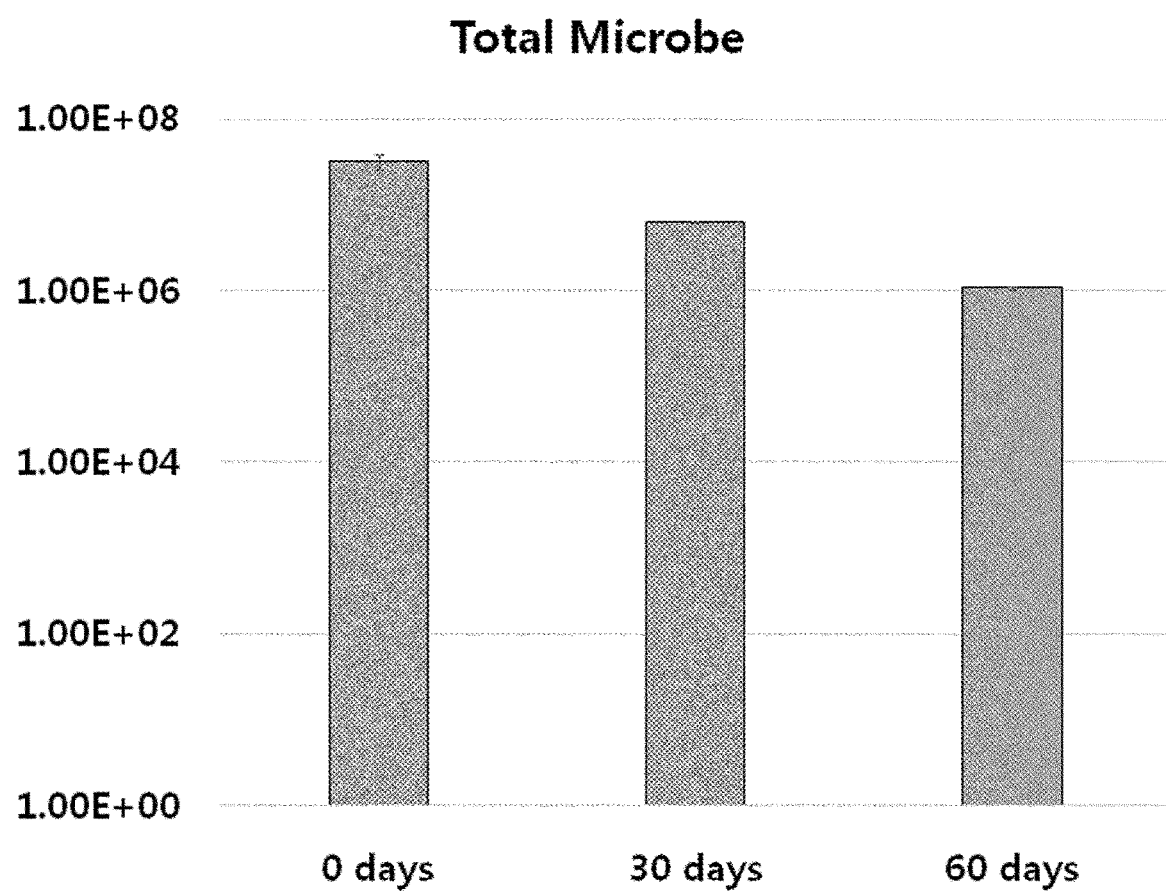
FIG. 18 shows the population of a combination of *Methylobacterium aquaticum* and *Methylobacterium komagatae* on a jig.
Figure 19:
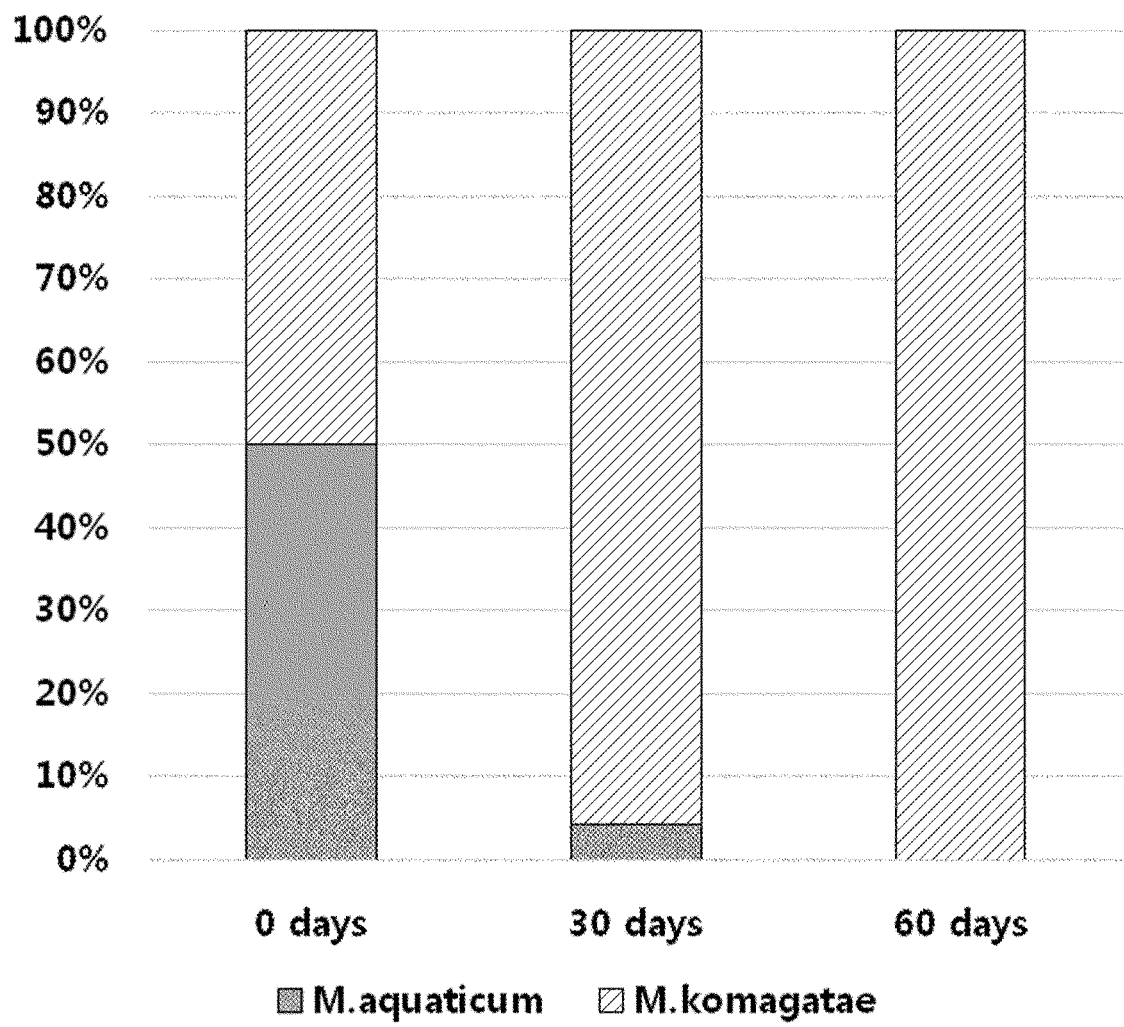
FIG. 19 shows the change in the population of a combination of *Methylobacterium aquaticum* and *Methylobacterium komagatae* on a jig measured by REP-PCR.

On the evaporator core coated with the two strains, the total bacterial count was $3.20 \times 10^7 \pm 6.56 \times 10^6$ CFU/g fin. The total bacterial count on the evaporator core was $6.23 \times 10^6 \pm 1.99 \times 10^5$ CFU/g fin after 30 days and $1.08 \times 10^6 \pm 4.36 \times 10^4$ CFU/g fin after 60 days (FIG. 18). Even though the evaporator core was exposed to the outdoor environment, no exogenous microorganism other than the colony of *Methylobacterium* sp. was detected after 60 days. When the detected microorganisms were identified by REP-PCR, the ratio of the strains was 1:1 at time 0. After 30 days, *Methylobacterium aquaticum* was decreased to 4.2% and, after 60 days, only *Methylobacterium komagatae* was detected (FIG. 19).

Conclusion

The 11 odorless microorganism species isolated from the evaporator core were divided into 4 groups based on morphological characteristics. The 11 microorganism species were identified as different species through 16S rDNA sequencing.

The microorganisms identified by 16S rDNA sequencing were subjected to REP-PCR and were found to be 11 different REP-PCR groups.

After conducting sensory evaluation of the individual strains after coating on an evaporator core, 8 microorganisms which generated relatively less offensive odors, *Methylobacterium aquaticum*, *Methylobacterium platani*, *Acinetobacter johnsonii*, *Brevibacillus invocatus*, *Leifsonia soli*, *Pseudomonas nitroreducens*, *Sphingomonas aquatilis* and *Methylobacterium komagatae*, were selected finally.

Sensory evaluation was conducted for 14 combinations prepared from the selected 8 microorganism species. As a result, a total of 10 combinations were selected for the final survival test. Among them, 4 combinations consisted of 5 strains, 4 combinations consisted of 4 strains, 1 combination consisted of 3 combinations and 1 combination consisted of 2 strains, including 2 common strains. Because *Methylobacterium platani* was found to be unsuitable, 6 additional combinations were prepared and subjected to survival evaluation for 30 days. As a result, *Methylobacterium aquaticum* and *Methylobacterium komagatae* were selected as common strains. A combination consisting only of the two common strains *Methylobacterium aquaticum* and *Methylobacterium komagatae* was subjected to survival evaluation for 90 days. As a result of conducting survival evaluation for 90 days under a laboratory condition, the combination maintained a similar population as that at the time of coating. In addition, an evaporator core coated with the combination of microorganisms was installed on a jig of a vehicle roof and survivability was evaluated after exposure to outdoor air. As a result, the total bacterial count was maintained at $10^6$ CFU/g fin and no exogenous microorganism was detected.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM ||
|---|---|
| Identification reference given by the DEPOSITOR : *Methylobacterium aquaticum* HKMC-1 | Accession number given by the INTERNATIONAL DEPOSITARY AUTHORITY: KCCM11325P |
| II. SCIENTIFIC DESCRIPTION AND/OR PROPOSED TAXONOMIC DESIGNATION ||
| The microorganism identified under I above was accompanied by: <br> ☐ a scientific description <br> ☐ a proposed taxonomic designation <br> (Mark with a cross where applicable) ||
| III. RECEIPT AND ACCEPTANCE ||
| This International Depositary Authority accepts the microorganism identified under I above, which was received by it on November. 14. 2012. (date of the original deposit)¹ ||
| IV. INTERNATIONAL DEPOSITARY AUTHORITY ||
| Name : Korean Culture Center of Microorganisms <br><br> Address : 361-221, Yurim B/D <br> Hongje-1-dong <br> Seodaemun-gu <br> SEOUL 120-091 <br> Republic of Korea | Signature(s) of person(s) having the power to represent the International Depositary Authority or of authorized official(s): <br><br> Date: November. 14. 2012. |

¹ Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                 Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
    12, Heolleung-ro, Seocho-gu,
    Seoul 137-938
    Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : *Methylobacterium brachiatum* HKMC-2 | Accession number given by the INTERNATIONAL DEPOSITARY AUTHORITY: KCCM11326P |
| II. SCIENTIFIC DESCRIPTION AND/OR PROPOSED TAXONOMIC DESIGNATION | |
| The microorganism identified under I above was accompanied by:<br>☐ a scientific description<br>☐ a proposed taxonomic designation<br>(Mark with a cross where applicable) | |
| III. RECEIPT AND ACCEPTANCE | |
| This International Depositary Authority accepts the microorganism identified under I above, which was received by it on November. 14. 2012. (date of the original deposit)[1] | |
| IV. INTERNATIONAL DEPOSITARY AUTHORITY | |
| Name : Korean Culture Center of Microorganisms<br>Address : 361-221, Yurim B/D<br>    Hongje-1-dong<br>    Seodaemun-gu<br>    SEOUL 120-091<br>    Republic of Korea | Signature(s) of person(s) having the power to represent the International Depositary Authority or of authorized official(s):<br><br>Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                           Sole page

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : *Methylobacterium platani* HKMC-3 | Accession number given by the INTERNATIONAL DEPOSITARY AUTHORITY: KCCM11327P |
| II. SCIENTIFIC DESCRIPTION AND/OR PROPOSED TAXONOMIC DESIGNATION | |
| The microorganism identified under I above was accompanied by: <br> ☐ a scientific description <br> ☐ a proposed taxonomic designation <br> (Mark with a cross where applicable) | |
| III. RECEIPT AND ACCEPTANCE | |
| This International Depositary Authority accepts the microorganism identified under I above, which was received by it on November. 14. 2012. (date of the original deposit)[1] | |
| IV. INTERNATIONAL DEPOSITARY AUTHORITY | |
| Name : Korean Culture Center of Microorganisms <br><br> Address : 361-221, Yurim B/D <br> Hongje-1-dong <br> Seodaemun-gu <br> SEOUL 120-091 <br> Republic of Korea | Signature(s) of person(s) having the power to represent the International Depositary Authority or of authorized official(s): <br><br> Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                 Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : *Acinetobacter johnsonii* HKMC-4 | Accession number given by the INTERNATIONAL DEPOSITARY AUTHORITY: KCCM11328P |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on November. 14. 2012. (date of the original deposit)[1] |

| IV. INTERNATIONAL DEPOSITARY AUTHORITY | |
|---|---|
| Name : Korean Culture Center of Microorganisms <br><br> Address : 361-221, Yurim B/D <br> Hongje-1-dong <br> Seodaemun-gu <br> SEOUL 120-091 <br> Republic of Korea | Signature(s) of person(s) having the power to represent the International Depositary Authority or of authorized official(s): <br><br> Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                                                       Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM ||
|---|---|
| Identification reference given by the DEPOSITOR : *Bacillus vietnamensis* HKMC-5 | Accession number given by the INTERNATIONAL DEPOSITARY AUTHORITY: KCCM11329P |
| II. SCIENTIFIC DESCRIPTION AND/OR PROPOSED TAXONOMIC DESIGNATION ||
| The microorganism identified under I above was accompanied by: ☐ a scientific description  ☐ a proposed taxonomic designation  (Mark with a cross where applicable) ||
| III. RECEIPT AND ACCEPTANCE ||
| This International Depositary Authority accepts the microorganism identified under I above, which was received by it on November. 14, 2012. (date of the original deposit)[1] ||
| IV. INTERNATIONAL DEPOSITARY AUTHORITY ||
| Name : Korean Culture Center of Microorganisms  Address : 361-221, Yurim B/D  Hongje-1-dong  Seodaemun-gu  SEOUL 120-091  Republic of Korea | Signature(s) of person(s) having the power to represent the International Depositary Authority or of authorized official(s):  Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                          Sole page

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : *Brevibacillus invocatus* HKMC-6 | Accession number given by the INTERNATIONAL DEPOSITARY AUTHORITY: KCCM11330P |
| II. SCIENTIFIC DESCRIPTION AND/OR PROPOSED TAXONOMIC DESIGNATION | |
| The microorganism identified under I above was accompanied by:<br>☐ a scientific description<br>☐ a proposed taxonomic designation<br>(Mark with a cross where applicable) | |
| III. RECEIPT AND ACCEPTANCE | |
| This International Depositary Authority accepts the microorganism identified under I above, which was received by it on November. 14. 2012. (date of the original deposit)[1] | |
| IV. INTERNATIONAL DEPOSITARY AUTHORITY | |
| Name : Korean Culture Center of Microorganisms<br><br>Address : 361-221, Yurim B/D<br>Hongje-1-dong<br>Seodaemun-gu<br>SEOUL 120-091<br>Republic of Korea | Signature(s) of person(s) having the power to represent the International Depositary Authority or of authorized official(s):<br><br>Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                   Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: *Deinococcus ficus* HKMC-7 | Accession number given by the INTERNATIONAL DEPOSITARY AUTHORITY: KCCM11331P |
| II. SCIENTIFIC DESCRIPTION AND/OR PROPOSED TAXONOMIC DESIGNATION | |
| The microorganism identified under I above was accompanied by:<br>☐ a scientific description<br>☐ a proposed taxonomic designation<br>(Mark with a cross where applicable) | |
| III. RECEIPT AND ACCEPTANCE | |
| This International Depositary Authority accepts the microorganism identified under I above, which was received by it on November. 14. 2012. (date of the original deposit)[1] | |
| IV. INTERNATIONAL DEPOSITARY AUTHORITY | |
| Name : Korean Culture Center of Microorganisms<br><br>Address : 361-221, Yurim B/D<br>Hongje-1-dong<br>Seodaemun-gu<br>SEOUL 120-091<br>Republic of Korea | Signature(s) of person(s) having the power to represent the International Depositary Authority or of authorized official(s):<br><br>Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4          Sole page

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM ||
|---|---|
| Identification reference given by the DEPOSITOR: *Leifsonia soli* HKMC-8 | Accession number given by the INTERNATIONAL DEPOSITARY AUTHORITY: KCCM11332P |
| II. SCIENTIFIC DESCRIPTION AND/OR PROPOSED TAXONOMIC DESIGNATION ||
| The microorganism identified under I above was accompanied by: <br> ☐ a scientific description <br> ☐ a proposed taxonomic designation <br> (Mark with a cross where applicable) ||
| III. RECEIPT AND ACCEPTANCE ||
| This International Depositary Authority accepts the microorganism identified under I above, which was received by it on November. 14. 2012. (date of the original deposit)[1] ||
| IV. INTERNATIONAL DEPOSITARY AUTHORITY ||
| Name : Korean Culture Center of Microorganisms <br><br> Address : 361-221, Yurim B/D <br> Hongje-1-dong <br> Seodaemun-gu <br> SEOUL 120-091 <br> Republic of Korea | Signature(s) of person(s) having the power to represent the International Depositary Authority or of authorized official(s): <br><br> Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 Sole page

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : <br> *Pseudomonas nitroreducens* HKMC-9 | Accession number given by the INTERNATIONAL DEPOSITARY AUTHORITY: <br> KCCM11333P |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on November. 14. 2012. (date of the original deposit)¹ |

| IV. INTERNATIONAL DEPOSITARY AUTHORITY | |
|---|---|
| Name : Korean Culture Center of Microorganisms <br><br> Address : 361-221, Yurim B/D <br> Hongje-1-dong <br> Seodaemun-gu <br> SEOUL 120-091 <br> Republic of Korea | Signature(s) of person(s) having the power to represent the International Depositary Authority or of authorized official(s): <br><br> Date: November. 14. 2012. |

¹ Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                                        Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM ||
|---|---|
| Identification reference given by the DEPOSITOR: *Sphingomonas aquatilis* HKMC 10 | Accession number given by the INTERNATIONAL DEPOSITARY AUTHORITY: KCCM11334P |
| II. SCIENTIFIC DESCRIPTION AND/OR PROPOSED TAXONOMIC DESIGNATION ||
| The microorganism identified under I above was accompanied by:<br>☐ a scientific description<br>☐ a proposed taxonomic designation<br>(Mark with a cross where applicable) ||
| III. RECEIPT AND ACCEPTANCE ||
| This International Depositary Authority accepts the microorganism identified under I above, which was received by it on November. 14. 2012. (date of the original deposit)[1] ||
| IV. INTERNATIONAL DEPOSITARY AUTHORITY ||
| Name : Korean Culture Center of Microorganisms<br><br>Address : 361-221, Yurim B/D<br>Hongje-1-dong<br>Seodaemun-gu<br>SEOUL 120-091<br>Republic of Korea | Signature(s) of person(s) having the power to represent the International Depositary Authority or of authorized official(s):<br><br>Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                                           Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: HYUNDAI MOTOR COMPANY
12, Heolleung-ro, Seocho-gu,
Seoul 137-938
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: *Methylobacterium komagatae* HKMC-11 | Accession number given by the INTERNATIONAL DEPOSITARY AUTHORITY: KCCM11335P |
| II. SCIENTIFIC DESCRIPTION AND/OR PROPOSED TAXONOMIC DESIGNATION | |
| The microorganism identified under I above was accompanied by:<br>☐ a scientific description<br>☐ a proposed taxonomic designation<br>(Mark with a cross where applicable) | |
| III. RECEIPT AND ACCEPTANCE | |
| This International Depositary Authority accepts the microorganism identified under I above, which was received by it on November. 14. 2012. (date of the original deposit)[1] | |
| IV. INTERNATIONAL DEPOSITARY AUTHORITY | |
| Name: Korean Culture Center of Microorganisms<br><br>Address: 361-221, Yurim B/D<br>Hongje-1-dong<br>Seodaemun-gu<br>SEOUL 120-091<br>Republic of Korea | Signature(s) of person(s) having the power to represent the International Depositary Authority or of authorized official(s):<br><br>Date: November. 14. 2012. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                                             Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938,
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM ||
|---|---|
| Identification reference given by the DEPOSITOR : <br> *Deinococcus apachensis* HKMC-12 | Accession number given by the INTERNATIONAL DEPOSITARY AUTHORITY: <br> KCCM11499P |
| II. SCIENTIFIC DESCRIPTION AND/OR PROPOSED TAXONOMIC DESIGNATION ||
| The microorganism identified under I above was accompanied by: <br> ☐ a scientific description <br> ☐ a proposed taxonomic designation <br> (Mark with a cross where applicable) ||
| III. RECEIPT AND ACCEPTANCE ||
| This International Depositary Authority accepts the microorganism identified under I above, which was received by it on December. 10. 2013. (date of the original deposit)[1] ||
| IV. INTERNATIONAL DEPOSITARY AUTHORITY ||
| Name : Korean Culture Center of Microorganisms <br><br> Address : Yurim B/D <br> 45, Hongjenae-2ga-gil <br> Seodaemun-gu <br> SEOUL 120-861 <br> Republic of Korea | Signature(s) of person(s) having the power to represent the International Depositary Authority or of authorized official(s): <br><br> Date: December. 10. 2013. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                                  Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. HYUNDAI MOTOR COMPANY
12, Heolleung-ro, Seocho-gu,
Seoul 137-938,
Republic of Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR : *Flavobacterium oceanosedimentum* HKMC-13 | Accession number given by the INTERNATIONAL DEPOSITARY AUTHORITY: KCCM11500P |
| II. SCIENTIFIC DESCRIPTION AND/OR PROPOSED TAXONOMIC DESIGNATION | |
| The microorganism identified under I above was accompanied by: <br> ☐ a scientific description <br> ☐ a proposed taxonomic designation <br> (Mark with a cross where applicable) | |
| III. RECEIPT AND ACCEPTANCE | |
| This International Depositary Authority accepts the microorganism identified under I above, which was received by it on December. 10. 2013. (date of the original deposit)[1] | |
| IV. INTERNATIONAL DEPOSITARY AUTHORITY | |
| Name : Korean Culture Center of Microorganisms <br><br> Address : Yurim B/D <br> 45, Hongjenae-2ga-gil <br> Seodaemun-gu <br> SEOUL 120-861 <br> Republic of Korea | Signature(s) of person(s) having the power to represent the International Depositary Authority or of authorized official(s) : <br><br> Date: December. 10. 2013. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                                                   Sole page

What is claimed is:

1. An evaporator core coated with a composition for preventing odors, wherein the composition comprises *Methylobacterium* or a culture thereof,
wherein the *Methylobacterium* is one or more *Methylobacterium* selected from the group consisting of *Methylobacterium komagatae*, *Methylobacterium aquaticum*, *Methylobacterium brachiatum* and *Methylobacterium platani*.

2. The evaporator core according to claim 1, wherein microorganisms in the composition are coated on the evaporator core at a concentration of $10^4$-$10^8$ CFU/g.

3. The evaporator core according to claim 2, wherein the microorganisms are coated using a microorganism culture having an optical density (O.D.) of 0.3-0.9.

4. The evaporator core according to claim 2, wherein the microorganisms in the composition form a biofilm on the evaporator core.

5. The evaporator core according to claim 1, wherein the *Methylobacterium* is one or more *Methylobacterium* selected from the group consisting of *Methylobacterium komagatae* HKMC-11 (KCCM11335P), *Methylobacterium aquaticum* HKMC-1 (KCCM11325P), *Methylobacterium brachiatum* HKMC-2 (KCCM11326P) and *Methylobacterium platani* HKMC-3 (KCCM11327P).

6. The evaporator core according to claim 1, wherein the composition further comprises one or more microorganism selected from the group consisting of *Acinetobacter johnsonii* HKMC-4 (KCCM11328P), *Bacillus vietnamensis* HKMC-5 (KCCM11329P), *Brevibacillus invocatus* HKMC-6 (KCCM11330P), *Deinococcus ficus* HKMC-7 (KCCM11331P), *Leifsonia soli* HKMC-8 (KCCM11332P), *Pseudomonas nitroreducens* HKMC-9 (KCCM11333P), *Sphingomonas aquatilis* HKMC-10 (KCCM11334P), *Deinococcus apachensis* HKMC-12 (KCCM11499P) and *Flavobacterium oceanosedimentum* HKMC-13 (KCCM11500P) or a culture thereof.

7. An air-conditioning system comprising an evaporator and a composition, wherein the evaporator is coated with the composition and the composition comprising *Methylobacterium* or a culture thereof,
wherein the *Methylobacterium* is one or more *Methylobacterium* selected from the group consisting of *Methylobacterium komagatae*, *Methylobacterium aquaticum*, *Methylobacterium brachiatum* and *Methylobacterium platani*.

8. The air-conditioning system according to claim 7, wherein the *Methylobacterium* is one or more *Methylobacterium* selected from the group consisting of *Methylobacterium komagatae* HKMC-11 (KCCM11335P), *Methylobacterium aquaticum* HKMC-1 (KCCM11325P), *Methylobacterium brachiatum* HKMC-2 (KCCM11326P) and *Methylobacterium platani* HKMC-3 (KCCM11327P).

9. The air-conditioning system according to claim 7, wherein the composition further comprises one or more microorganism selected from the group consisting of *Acinetobacter johnsonii* HKMC-4 (KCCM11328P), *Bacillus vietnamensis* HKMC-5 (KCCM11329P), *Brevibacillus invocatus* HKMC-6 (KCCM11330P), *Deinococcus ficus* HKMC-7 (KCCM11331P), *Leifsonia soli* HKMC-8 (KCCM11332P), *Pseudomonas nitroreducens* HKMC-9 (KCCM11333P), *Sphingomonas aquatilis* HKMC-10 (KCCM11334P), *Deinococcus apachensis* HKMC-12 (KCCM11499P) and *Flavobacterium oceanosedimentum* HKMC-13 (KCCM11500P) or a culture thereof.

10. The air-conditioning system according to claim 7, wherein microorganisms in the composition are coated on the evaporator core at a concentration of $10^4$-$10^8$ CFU/g.

11. The air-conditioning system according to claim 10, wherein the microorganisms are coated using a microorganism culture having an optical density (O.D.) of 0.3-0.9.

12. The air-conditioning system according to claim 10, wherein the microorganisms in the composition form a biofilm on the evaporator core.

\* \* \* \* \*